(12) United States Patent
Saito

(10) Patent No.: US 6,555,371 B1
(45) Date of Patent: Apr. 29, 2003

(54) SIALYLTRANSFERASE AND DNA ENCODING THE SAME

(75) Inventor: Masaki Saito, Tokyo (JP)

(73) Assignee: Seikagaku Kogyo Kabushiki Kaisha, Tokyo (JP)

( * ) Notice: Subject to any disclaimer, the term of this patent is extended or adjusted under 35 U.S.C. 154(b) by 0 days.

(21) Appl. No.: 09/425,488

(22) Filed: Oct. 22, 1999

Related U.S. Application Data

(63) Continuation-in-part of application No. 09/112,563, filed on Jul. 9, 1998, now abandoned.

(30) Foreign Application Priority Data

Jul. 9, 1997 (JP) ............................................. 9-184184
May 27, 1999 (JP) ........................................... 11-148603

(51) Int. Cl.$^7$ ............................. C12N 15/54; C12N 9/10
(52) U.S. Cl. ..................... 435/325; 536/23.2; 536/23.1; 435/193; 435/252.3; 435/320.1
(58) Field of Search .............................. 536/23.1, 23.2; 435/193, 320.1, 252.3, 325

(56) References Cited

U.S. PATENT DOCUMENTS 6,280,989 B1 * 8/2001 Kapitonov et al. ......... 435/193

OTHER PUBLICATIONS

T. Osanai et al. "Glycolipid Sialytransferases are Enhanced During Neural Differentiation of Mouse Embryonic Carcinoma Cells, p.19". Biochem. Biophys. Res. Commun. 241(2): 327–333, Dec. 1997.*

M. Nakamura et al., Total Metabolic Flow of Glycosphingolipid Biosynthesis is Regulated By UDP–GlcNAc:lactosylceramide beta 1,3 N–Acetylglucosaminyltransferase and CMP–NeuAc:lactosylceramide alpha 2,3 Sialytransferase in Human Hematopoietic Cell Line HL, Nov. 1992.*

U. Preuss et al., "Purification and Characterization of CMP–N–Acetylneuraminic Acid:Lactosylceramide (alpha 2–3) Sialytransferase (GM3 synthase) From Rat Brain", J. Biol. Chem. 268(35): 26273–26278, Dec. 1993.*

GenBank Accession No. AB018048, Oct. 1998.*

GenBank Accession No. AB018356, Oct. 1998.*

D. Miyamoto et al. "Glycolipid Acceptor Specificity of a Human Gal(1–3/1–4) GlcNAc Alpha 2,3–Sialytransferase" Biochem. Biophys. Res. Commun. 217(3): 852–858. (Dec. 1995).*

K. Sasaki et al., "Expression Cloning of a Novel Galβ(1–3/1–4)GlcNAc Alpha 2,3–Sialytransferase Using Lectin Resistance Selection", J. Biol. Chem. 268(30): 22782–22787. (Oct. 1993).*

A. Ishii et al. "Expression Cloning and Functional Characterization of Human cDNA for Ganglioside GM3 Synthase", J.Biol. Chem 273(48): 31652–31655. (Nov. 1998).*

M.D. Adams et al. GenBank Accession No. AA386324. (Apr. 1997).*

K.W. Kim et al. GenBank Accession No. AF105026. (Feb. 1999).*

M. Marra et al. GenBank Accession No. AA208995. (Jan. 1997).*

M. Marra et al. GenBank Accession No. AA117276. (Nov. 1996).*

Lyla J. Melkerson, et al., Purification to Apparent Homogeneity by Immunoaffinity Chromatography and Partial Characterization of the $G_{M3}$ Ganglioside–forming Enzyme, CMP–Sialic Acid: Lactosylceramide α2, 3–Sialytransferase (SAT–1), from Rat Liver Golgi, The Journal of Biological Chemistry, vol. 266 No. 7, Issue of Mar. 5, pp. 4448–4457, 1991.

* cited by examiner

Primary Examiner—Rebecca E. Prouty
(74) Attorney, Agent, or Firm—Knobbe, Martens, Olson & Bear, LLP

(57) ABSTRACT

A sialyltransferase having the following physico-chemical properties:
(1) Activity:
transfers sialic acid from a sialic acid donor selectively to a 3-hydroxyl group of a galactose residue contained in lactosylceramide as a sialic acid acceptor to produce ganglioside $G_{M3}$;
(2) Optimal reaction pH:
6.0 to 7.0; and
(3) Inhibition and activation:
the activity increases at least 1.5 times with 10 mM of $Mn^{2+}$ as compared with the case in the absence thereof.

3 Claims, 5 Drawing Sheets

SIALYLMOTIF L

```
SAT-1     136 CKRCVVVGNG GILHGLELGH ALNQFDVVIR LNSAPV-EGY SEHVGNKTT 183
h2,3ST    117 CRRCVVVGNG HRLRNSSLGG VINKYDVVIR LNNAPV-AGY EGDVGSKTT 164
rSTX      154 FQTCAIVGNS GVLLNSGCGQ EIDTHSFVIR CNLAPV-WEY ARDVGLKTD 201
rST3N-1   156 CRRCIIVGNG GVLANKSLGS RIDDYDIVIR LNSAPV-KGF EKDVGSKTT 203
hST3N-2   113 CRRCVVVGNG HRLRNSSLGD AINKYDVVIR LNNAPV-AGY EGDVGSKTT 160
pST30-1   142 CRRCAVVGNS GNLKESYYGP QIDSHDFVLR MNKAPT-EGF EADVGSKTT 189
pST30-2   136 CRRCAVVGNS GNLKDSSYGP EIDSHDFVLR MNKAPT-VGF EADVGSRTT 183
mST4'     117 CRRCVVVGNG HRLRNSSLGG VINKYDVVIR LNNAPV-AGY EGDVGSKTT 164
hSAT4(a)  141 CRRCAVVGNS GNLRESSYGP EIDSKDFVLR MNKAPT-AGF EADVGTKTT 188
hST6N     181 WGRCAVVSSA GSLKSSQLGR EIDDHDAVLR FNGAPT-ANF QQDVGTKTT 228
rST6N     178 WQRCAVVSSA GSLKNSQLGR EIDNHDAVLR FNGAPT-DNF QQDVGSKTT 225
h2,8ST    120 LKKCAVVGNG GILKKSGCGR QIDEANFVMR CNLFPLSSEY TKDVGSKSQ 168
```

SIALYLMOTIF S

```
SAT-1     283 PTIGVIAVVL ATHLCDEVSL AGF 305
h2,3ST    259 PTTGLLAITL ALHLCDLVHI AGF 281
rSTX      293 PTTGLLMYTL ATRFCNQIYL YGF 315
rST3N-1   299 PTLGSVAVTM ALDGCDEVAV AGF 321
hST3N-2   255 PTTGLLAITL ALHLCDLVHI AGF 277
pST30-1   270 PSTGILSVIF SLHICDEVDL YGF 292
pST30-2   264 PSTGILSIIF SIHICDEVDL YGF 286
mST4'     259 PTTGLLAITL ALHLCDLVHI AGF 281
hSAT4(a)  267 PSTGILSVIE SMHVCDEVDL YGF 289
hST6N     321 PSSGMLGIII MMTLCDQVDI YEF 343
rST6N     318 PSSGMLGIII MMTLCDQVDI YEF 340
h2,8ST    258 LSTGLFLVSA ALGLCEEVAI YGF 280
```

FIG. 2

SIALYLMOTIF L

| | | | | | | | |
|---|---|---|---|---|---|---|---|
| SAT-1 | 136 | CRRCVVIGSG | GILHGLELGH | TLNQFDVVIR | LNSAPV-EGY | SEHVGNKTT | 183 |
| ST3N-1 | 157 | CRRCIIVGNG | GVLANKSLGS | RIDDYDIVVR | LNSAPV-KGF | EKDVGSKTT | 204 |
| ST3N-2 | 113 | CRRCVVVGNG | HRLRNSSLGD | AINKYDVVIR | LNNAPV-AGY | EGDVGSKTT | 160 |
| ST30-1 | 139 | CRRCAVVGNS | GNLRESSYGP | EIDSHDFVLR | MNKAPT-AGF | EADVGTKTT | 186 |
| ST30-2 | 149 | CRRCAVVGNS | GNLRGSGYGQ | DVDGHNFIMR | MNQAPT-VGF | EQDVGSRTT | 196 |
| SThM | 148 | CIRCAVVGNG | GILNGSRQGP | NIDAHDYVFR | LNGAVI-KGF | ERDVGTKTS | 195 |
| ST6N | 181 | WGRCAVVSSA | GSLKSSQLGR | EIDDHDAVLR | FNGAPT-ANF | QQDVGTKTT | 228 |
| SAT-II | 120 | LKKCAVVGNG | GILKKSGCGR | QIDEANFVMR | CNLFPLSSEY | TKDVGSKSQ | 168 |
| STX | 154 | FGTCAIVGNS | GVLLNSGCGQ | EIDAHSFVIR | CNLAPV-QEY | ARDVGLKTD | 201 |
| ST8SiaIII | 159 | YNICAVVGNS | GILTFIQCGR | EIDKSDFVFR | CNFAPS-EAF | QRDVGRKTN | 206 |
| PST-1 | 139 | FKTCAVVGNS | GILLDSECGK | EIDSHNFVIR | CNLAPV-VEF | AADVGTKSD | 186 |
| ST8SiaV | 161 | FKKCAVVGNG | GILKNSRCGR | EINSADFVFR | CNLPPISEKY | TMDVGVKTD | 209 |

SIALYLMOTIF S

| | | | | | |
|---|---|---|---|---|---|
| SAT-1 | 282 | PTIGVIAVVL | ATHLCDEVSL | AGF | 305 |
| ST3N-1 | 300 | PTLGSVAVTM | ALHGCDEVAV | AGF | 322 |
| ST3N-2 | 255 | PTTGLLAITL | ALHLCDLVHI | AGF | 277 |
| ST30-1 | 267 | PSTGILSVIF | SMHVCDEVDL | YGF | 289 |
| ST30-2 | 277 | PSTGMLVLFF | ALHVCDEVNV | YGF | 299 |
| SThM | 303 | PSTGALMLLT | ALHTCDQVSA | YGF | 325 |
| ST6N | 321 | PSSGMLGIII | MMTLCDQVDI | YEF | 343 |
| SAT-II | 258 | LSTGLFLVSA | ALGLCEEVAI | YGF | 280 |
| STX | 293 | PTTGLLMYTL | ATRFCKQIYL | YGF | 315 |
| ST8SiaIII | 299 | LSTGILMYTL | ASAICEEIHL | YGF | 321 |
| PST-1 | 278 | PSTGLLMYTL | ATRFCDEIHL | YGF | 300 |
| ST8SiaV | 299 | ISTGLILVTA | ALELCEEVHL | FGF | 321 |

*FIG. 4*

SEQUENCE LISTING

<160> NUMBER OF SEQ ID NOS: 12

<210> SEQ ID NO 1
<211> LENGTH: 2121
<212> TYPE: DNA
<213> ORGANISM: Mus musculus
<220> FEATURE:
<221> NAME/KEY: CDS
<222> LOCATION: 202..1278
<221> NAME/KEY: misc_feature
<222> LOCATION: 247..288
<223> OTHER INFORMATION: transmembrane domain
<221> NAME/KEY: misc_feature
<222> LOCATION: 871..879
<223> OTHER INFORMATION: potential N-glycosylation site
<221> NAME/KEY: misc_feature
<222> LOCATION: 1201..1209
<223> OTHER INFORMATION: potential N-glycosylation site
<221> NAME/KEY: misc_feature
<222> LOCATION: 616..750
<223> OTHER INFORMATION: sialyl-motif
<221> NAME/KEY: misc_feature
<222> LOCATION: 1048..1116
<223> OTHER INFORMATION: sialyl-motif

<400> SEQUENCE: 1

```
cccgggctgg cggcttgcca gcgctccctc cctagcatgc acacagaggc ggtgggcggc        60
gcggcgcgga ggccccagaa gctgcgaagc caagcagcgg cacctgcctg ccgagcaatg       120
ccaagtgagt tcacctctgc aaagctgaga agtgattgct caaggacctc cctgcaatgg       180
tacacccgaa cccagcacaa g atg aga aga ccc agc ttg tta ata aaa gac        231
                         Met Arg Arg Pro Ser Leu Leu Ile Lys Asp
                           1               5                  10 atc tgc aag tgc acg ttg gtt gca ttt gga gtc tgg ctc ctg tac atc        279
Ile Cys Lys Cys Thr Leu Val Ala Phe Gly Val Trp Leu Leu Tyr Ile
             15                  20                  25 ctc att ttg aat tac acc gct gaa gaa tgt gac atg aaa aga atg cac        327
Leu Ile Leu Asn Tyr Thr Ala Glu Glu Cys Asp Met Lys Arg Met His
         30                  35                  40 tat gtg gac cct gac cgg ata aag aga gct cag agc tat gct cag gaa        375
Tyr Val Asp Pro Asp Arg Ile Lys Arg Ala Gln Ser Tyr Ala Gln Glu
     45                  50                  55 gtc ttg cag aag gaa tgt cgg ccc agg tac gcg aag acg gct atg gct        423
Val Leu Gln Lys Glu Cys Arg Pro Arg Tyr Ala Lys Thr Ala Met Ala
 60                  65                  70 ctg tta ttt gag gac agg tac agc atc aac ttg gag cct ttt gtg cag        471
Leu Leu Phe Glu Asp Arg Tyr Ser Ile Asn Leu Glu Pro Phe Val Gln
 75                  80                  85                  90 aag gtc ccc acg gcc agt gaa gct gag ctc aag tat gac ccg cct ttt        519
Lys Val Pro Thr Ala Ser Glu Ala Glu Leu Lys Tyr Asp Pro Pro Phe
                 95                 100                 105 gga ttc cgg aag ttc tcc agt aaa gtc cag agc ctc ttg gat atg ctg        567
Gly Phe Arg Lys Phe Ser Ser Lys Val Gln Ser Leu Leu Asp Met Leu
             110                 115                 120 ccc gaa cat gac ttt cct gaa cac ttg aga gcc aag gcc tgc aag cgc        615
Pro Glu His Asp Phe Pro Glu His Leu Arg Ala Lys Ala Cys Lys Arg
         125                 130                 135 tgt gtg gtt gtt ggg aac ggg ggc atc ctg cac gga cta gag ctg ggt        663
Cys Val Val Val Gly Asn Gly Gly Ile Leu His Gly Leu Glu Leu Gly
     140                 145                 150 cac gcc ctc aac cag ttc gat gtg gta ata agg ttg aac agt gcg cca        711
His Ala Leu Asn Gln Phe Asp Val Val Ile Arg Leu Asn Ser Ala Pro
155                 160                 165                 170
```

-continued

| | | |
|---|---|---|
| gtt gag ggt tac tct gaa cac gtt ggg aat aaa act act ata agg atg<br>Val Glu Gly Tyr Ser Glu His Val Gly Asn Lys Thr Thr Ile Arg Met<br>              175                     180                   185 | | 759 |
| act tac cca gag ggt gcg cca ctg tcg gac gtt gaa tac tac gcc aat<br>Thr Tyr Pro Glu Gly Ala Pro Leu Ser Asp Val Glu Tyr Tyr Ala Asn<br>          190                     195                   200 | | 807 |
| gat ttg ttc gtt act gtt tta ttt aag agt gtt gat ttc aag tgg ctt<br>Asp Leu Phe Val Thr Val Leu Phe Lys Ser Val Asp Phe Lys Trp Leu<br>         205                    210                 215 | | 855 |
| caa gca atg gta aaa aat gaa agc ctg ccc ttt tgg gtt cgc ctc ttc<br>Gln Ala Met Val Lys Asn Glu Ser Leu Pro Phe Trp Val Arg Leu Phe<br>220                   225                 230 | | 903 |
| ttt tgg aag caa gtg gca gaa aaa gtc cca ctc cag cca aag cac ttc<br>Phe Trp Lys Gln Val Ala Glu Lys Val Pro Leu Gln Pro Lys His Phe<br>235                   240                 245                 250 | | 951 |
| agg att ttg aac cca gtt atc atc aaa gaa act gcc ttc gac atc ctt<br>Arg Ile Leu Asn Pro Val Ile Ile Lys Glu Thr Ala Phe Asp Ile Leu<br>              255                     260                 265 | | 999 |
| cag tac tca gag cct cag tca aga ttc tgg ggc cat gat aag aac atc<br>Gln Tyr Ser Glu Pro Gln Ser Arg Phe Trp Gly His Asp Lys Asn Ile<br>         270                     275                 280 | | 1047 |
| ccc acg atc ggc gtc att gcc gtt gtc ttg gct aca cat ctg tgt gat<br>Pro Thr Ile Gly Val Ile Ala Val Val Leu Ala Thr His Leu Cys Asp<br>         285                     290                 295 | | 1095 |
| gaa gtc agc ctg gca ggc ttt ggc tac gac ctc agt caa ccc agg acc<br>Glu Val Ser Leu Ala Gly Phe Gly Tyr Asp Leu Ser Gln Pro Arg Thr<br>300                   305                 310 | | 1143 |
| cct ctg cac tac ttt gac agt cag tgc atg ggc gcc atg cac tgg cag<br>Pro Leu His Tyr Phe Asp Ser Gln Cys Met Gly Ala Met His Trp Gln<br>315                   320                 325                 330 | | 1191 |
| gtc atg cac aat gtg acc aca gag acc aag ttc ctc ctg aag ctc ctc<br>Val Met His Asn Val Thr Thr Glu Thr Lys Phe Leu Leu Lys Leu Leu<br>              335                     340                 345 | | 1239 |
| aag gag ggc gtg gtg gag gac ctc agc ggc ggc atc cac tgagaactcg<br>Lys Glu Gly Val Val Glu Asp Leu Ser Gly Gly Ile His<br>         350                     355 | | 1288 |
| gaacacggca aacctcaccc agcaccgcag ctgagagcgt ggtgagcagc ctccacaggg | | 1348 |
| acttcaccct gcagctgctt cgatgtgcag ctagtgtttt caaactccac attttttta | | 1408 |
| aaaaaggaaa agaaagaaca acagcaacaa caaaagctct gctctgtgca cctcttcgtc | | 1468 |
| ctatttattt gaagtcagtg ttggattttg cacagttttg taagttaatc ttaagaatgg | | 1528 |
| gattggaagg acttttcaaa gagaattgta tagtttattg ttttttaagg aagtaattta | | 1588 |
| atttgcagaa actgtacaca cgtactctgc tcaggtgttg aggtgggagg agagggctt | | 1648 |
| ctggcccctg gatgatggct gtgatgcccg atactgggt ctgctgctct gtttggtaga | | 1708 |
| actgatggca gagaaacttc ctgcctccag gataaagggc ttactcatca cctctggcag | | 1768 |
| ctgctagaca agttcataac ccctttctgc tagtccatct gccagctggc tcgcaggact | | 1828 |
| caggcagggc agctgtcccg gaggctgctg gttggtgagc cactgtcagc tgagcgccgt | | 1888 |
| gatgttgccc cagggtggaa gaagccacac ttcctacact gtcagggcac ttttaaactt | | 1948 |
| ctggaggggt gtgtgtgtgt gtgtgtgtgt gtgtgtgtgt gtgtgtgtgt gtgtgtgtgt | | 2008 |
| gttcattctg cccttccaaa tcatctaagt gttatttaag gcactctgct gtttgtatga | | 2068 |
| gatggttcat agaaattatg acaaagcctt tgttatccag gccatgggaa gag | | 2121 |

<210> SEQ ID NO 2

```
<211> LENGTH: 359
<212> TYPE: PRT
<213> ORGANISM: Mus musculus

<400> SEQUENCE: 2

Met Arg Arg Pro Ser Leu Leu Ile Lys Asp Ile Cys Lys Cys Thr Leu
 1               5                  10                  15

Val Ala Phe Gly Val Trp Leu Leu Tyr Ile Leu Ile Leu Asn Tyr Thr
                20                  25                  30

Ala Glu Glu Cys Asp Met Lys Arg Met His Tyr Val Asp Pro Asp Arg
             35                  40                  45

Ile Lys Arg Ala Gln Ser Tyr Ala Gln Glu Val Leu Gln Lys Glu Cys
 50                  55                  60

Arg Pro Arg Tyr Ala Lys Thr Ala Met Ala Leu Leu Phe Glu Asp Arg
 65                  70                  75                  80

Tyr Ser Ile Asn Leu Glu Pro Phe Val Gln Lys Val Pro Thr Ala Ser
                 85                  90                  95

Glu Ala Glu Leu Lys Tyr Asp Pro Pro Phe Gly Phe Arg Lys Phe Ser
            100                 105                 110

Ser Lys Val Gln Ser Leu Leu Asp Met Leu Pro Glu His Asp Phe Pro
        115                 120                 125

Glu His Leu Arg Ala Lys Ala Cys Lys Arg Cys Val Val Val Gly Asn
    130                 135                 140

Gly Gly Ile Leu His Gly Leu Glu Leu Gly His Ala Leu Asn Gln Phe
145                 150                 155                 160

Asp Val Val Ile Arg Leu Asn Ser Ala Pro Val Glu Gly Tyr Ser Glu
                165                 170                 175

His Val Gly Asn Lys Thr Thr Ile Arg Met Thr Tyr Pro Glu Gly Ala
            180                 185                 190

Pro Leu Ser Asp Val Glu Tyr Tyr Ala Asn Asp Leu Phe Val Thr Val
        195                 200                 205

Leu Phe Lys Ser Val Asp Phe Lys Trp Leu Gln Ala Met Val Lys Asn
    210                 215                 220

Glu Ser Leu Pro Phe Trp Val Arg Leu Phe Phe Trp Lys Gln Val Ala
225                 230                 235                 240

Glu Lys Val Pro Leu Gln Pro Lys His Phe Arg Ile Leu Asn Pro Val
                245                 250                 255

Ile Ile Lys Glu Thr Ala Phe Asp Ile Leu Gln Tyr Ser Glu Pro Gln
            260                 265                 270

Ser Arg Phe Trp Gly His Asp Lys Asn Ile Pro Thr Ile Gly Val Ile
        275                 280                 285

Ala Val Val Leu Ala Thr His Leu Cys Asp Glu Val Ser Leu Ala Gly
    290                 295                 300

Phe Gly Tyr Asp Leu Ser Gln Pro Arg Thr Pro Leu His Tyr Phe Asp
305                 310                 315                 320

Ser Gln Cys Met Gly Ala Met His Trp Gln Val Met His Asn Val Thr
                325                 330                 335

Thr Glu Thr Lys Phe Leu Leu Lys Leu Leu Lys Glu Gly Val Val Glu
            340                 345                 350

Asp Leu Ser Gly Gly Ile His
        355

<210> SEQ ID NO 3
<211> LENGTH: 17
<212> TYPE: DNA
```

-continued

```
<213> ORGANISM: Artifical Sequence
<220> FEATURE:
<223> OTHER INFORMATION: Synthetic DNA as 5'-primer

<400> SEQUENCE: 3
atgaaaagaa tgcacta                                                    17

<210> SEQ ID NO 4
<211> LENGTH: 20
<212> TYPE: DNA
<213> ORGANISM: Artificial Sequence
<220> FEATURE:
<223> OTHER INFORMATION: Synthetic DNA as 3'-primer

<400> SEQUENCE: 4
tcagtggatg ccgccgctga                                                 20

<210> SEQ ID NO 5
<211> LENGTH: 18
<212> TYPE: PRT
<213> ORGANISM: Mus musculus

<400> SEQUENCE: 5

Leu Leu Lys Leu Leu Lys Glu Gly Val Val Glu Asp Leu Ser Gly Gly
  1               5                  10                  15

Ile His

<210> SEQ ID NO 6
<211> LENGTH: 48
<212> TYPE: PRT
<213> ORGANISM: Mus musculus

<400> SEQUENCE: 6

Cys Lys Arg Cys Val Val Gly Asn Gly Gly Ile Leu His Gly Leu
  1               5                  10                  15

Glu Leu Gly His Ala Leu Asn Gln Phe Asp Val Val Ile Arg Leu Asn
                 20                  25                  30

Ser Ala Pro Val Glu Gly Tyr Ser Glu His Val Gly Asn Lys Thr Thr
             35                  40                  45

<210> SEQ ID NO 7
<211> LENGTH: 2359
<212> TYPE: DNA
<213> ORGANISM: Homo sapiens
<220> FEATURE:
<221> NAME/KEY: CDS
<222> LOCATION: (278)..(1363)

<400> SEQUENCE: 7
ctgagcgggg gagcggcggc ccccagctga atgggcgcga gagcggcgct gggggcgggt      60
gggggcgcgg ggtaccgggc tggcggccgg ccggcgcccc ctcattagta tgcggacgaa     120
ggcggcgggc tgcgcggagc ggcgtcccct gcagccgcgg accgaggcag cggcggcacc     180
tgccggccga gcaatgccaa gtgagtacac ctatgtgaaa ctgagaagtg attgctcgag     240
gccttccctg caatggtaca cccgagctca aagcaag atg aga agg ccc agc ttg     295
                                        Met Arg Arg Pro Ser Leu
                                          1               5 tta tta aaa gac atc ctc aaa tgt aca ttg ctt gtg ttt gga gtg tgg       343
Leu Leu Lys Asp Ile Leu Lys Cys Thr Leu Leu Val Phe Gly Val Trp
         10                  15                  20 atc ctt tat atc ctc aag tta aat tat act act gaa gaa tgt gac atg       391
Ile Leu Tyr Ile Leu Lys Leu Asn Tyr Thr Thr Glu Glu Cys Asp Met
```

```
                    25                      30                      35
aaa aaa atg cat tat gtg gac cct gac cgt gta aag aga gct cag aaa        439
Lys Lys Met His Tyr Val Asp Pro Asp Arg Val Lys Arg Ala Gln Lys
        40                      45                      50 tat gct cag caa gtc ttg cag aag gaa tgt cgt ccc aag ttt gcc aag        487
Tyr Ala Gln Gln Val Leu Gln Lys Glu Cys Arg Pro Lys Phe Ala Lys
 55                      60                      65                      70 aca tca atg gcg ctg tta ttt gag cac agg tat agc gtg gac tta ctc        535
Thr Ser Met Ala Leu Leu Phe Glu His Arg Tyr Ser Val Asp Leu Leu
                75                      80                      85 cct ttt gtg cag aag gcc ccc aaa gac agt gaa gct gag tcc aag tac        583
Pro Phe Val Gln Lys Ala Pro Lys Asp Ser Glu Ala Glu Ser Lys Tyr
                        90                      95                     100 gat cct cct ttt ggg ttc cgg aag ttc tcc agt aaa gtc cag acc ctc        631
Asp Pro Pro Phe Gly Phe Arg Lys Phe Ser Ser Lys Val Gln Thr Leu
                105                     110                     115 ttg gaa ctc ttg cca gag cac gac ctc cct gaa cac ttg aaa gcc aag        679
Leu Glu Leu Leu Pro Glu His Asp Leu Pro Glu His Leu Lys Ala Lys
        120                     125                     130 acc tgt cgg cgc tgt gtg gtt att gga agc gga gga ata ctg cac gga        727
Thr Cys Arg Arg Cys Val Val Ile Gly Ser Gly Gly Ile Leu His Gly
135                     140                     145                     150 tta gaa ctg ggc cac acc ctg aac cag ttc gat gtt gtg ata agg tta        775
Leu Glu Leu Gly His Thr Leu Asn Gln Phe Asp Val Val Ile Arg Leu
                        155                     160                     165 aac agt gca cca gtt gag gga tat tca gaa cat gtt gga aat aaa act        823
Asn Ser Ala Pro Val Glu Gly Tyr Ser Glu His Val Gly Asn Lys Thr
                170                     175                     180 act ata agg atg act tat cca gag ggc gca cca ctg tct gac ctt gaa        871
Thr Ile Arg Met Thr Tyr Pro Glu Gly Ala Pro Leu Ser Asp Leu Glu
        185                     190                     195 tat tat tcc aat gac tta ttt gtt gct gtt tta ttt aag agt gtt gat        919
Tyr Tyr Ser Asn Asp Leu Phe Val Ala Val Leu Phe Lys Ser Val Asp
                200                     205                     210 ttc aac tgg ctt caa gca atg gta aaa aag gaa acc ctg cca ttc tgg        967
Phe Asn Trp Leu Gln Ala Met Val Lys Lys Glu Thr Leu Pro Phe Trp
215                     220                     225                     230 gta cga ctc ttc ttt tgg aag cag gtg gca gaa aaa atc cca ctg cag       1015
Val Arg Leu Phe Phe Trp Lys Gln Val Ala Glu Lys Ile Pro Leu Gln
                        235                     240                     245 cca aaa cat ttc agg att ttg aat cca gtt atc atc aaa gag act gcc       1063
Pro Lys His Phe Arg Ile Leu Asn Pro Val Ile Ile Lys Glu Thr Ala
                250                     255                     260 ttt gac atc ctt cag tac tca gag cct cag tca agg ttc tgg ggc cga       1111
Phe Asp Ile Leu Gln Tyr Ser Glu Pro Gln Ser Arg Phe Trp Gly Arg
        265                     270                     275 gat aag aac gtc ccc aca atc ggt gtc att gcc gtt gtc tta gcc aca       1159
Asp Lys Asn Val Pro Thr Ile Gly Val Ile Ala Val Val Leu Ala Thr
                280                     285                     290 cat ctg tgc gat gaa gtc agt ttg gcg ggt ttt gga tat gac ctc aat       1207
His Leu Cys Asp Glu Val Ser Leu Ala Gly Phe Gly Tyr Asp Leu Asn
295                     300                     305                     310 caa ccc aga aca cct ttg cac tac ttc gac agt caa tgc atg gct gct       1255
Gln Pro Arg Thr Pro Leu His Tyr Phe Asp Ser Gln Cys Met Ala Ala
                        315                     320                     325 atg aac ttt cag acc atg cat aat gtg aca acg gaa acc aag ttc ctc       1303
Met Asn Phe Gln Thr Met His Asn Val Thr Thr Glu Thr Lys Phe Leu
                330                     335                     340 tta aag ctg gtc aaa gag gga gtg gtg aaa gat ctc agt gga ggc att       1351
```

```
Leu Lys Leu Val Lys Glu Gly Val Val Lys Asp Leu Ser Gly Gly Ile
        345                 350                 355 gat cgt gaa ttt tgaacacaga aaacctcagt tgaaatgca actctaactc       1403
Asp Arg Glu Phe
        360 tgagagctgt ttttgacagc cttcttgatg tatttctcca tcctgcagat actttgaagt 1463 gcagctcatg tttttaactt ttaatttaaa aacacaaaaa aaattttagc tcttcccact 1523 tttttttttcc tatttatttg aggtcagtgt ttgttttttgc acaccattt gtaaatgaaa 1583 cttaagaatt gaattggaaa gacttctcaa agagaattgt atgtaacgat gttgtattga 1643 tttttaagaa agtaatttaa tttgtaaaac ttctgctcgt ttacactgca cattgaatac 1703 aggtaactaa ttggaaggag aggggaggtc actcttttga tggtggccct gaacctcatt 1763 ctggttccct gctgcgctgc ttggtgtgac ccacggagga tccactccca ggatgacgtg 1823 ctccgtagct ctgctgctga tactgggtct gcgatgcagc ggcgtgaggc ctgggctggt 1883 tggagaaggt cacaacccctt ctctgttggt ctgccttctg ctgaaagact cgagaaccaa 1943 ccagggaagc tgtcctggag gtccctggtc ggagagggac atagaatctg tgacctctga 2003 caactgtgaa gccaccctgg gctacagaaa ccacagtctt cccagcaatt attacaattc 2063 ttgaattcct tggggatttt ttactgcct ttcaaagcac ttaagtgtta gatctaacgt 2123 gttccagtgt ctgtctgagg tgacttaaaa aatcagaaca aaacttctat tatccagagt 2183 catgggagag tacacccttt ccaggaataa tgttttggga aacactgaaa tgaaatcttc 2243 ccagtattat aaattgtgta tttaaaaaaa agaaactttt ctgaatgcct acctggcggt 2303 gtataccagg cagtgtgcca gtttaaaaag atgaaaaaga ataaaaactt ttgagg       2359
```

<210> SEQ ID NO 8
<211> LENGTH: 362
<212> TYPE: PRT
<213> ORGANISM: Homo sapiens

<400> SEQUENCE: 8

```
Met Arg Arg Pro Ser Leu Leu Leu Lys Asp Ile Leu Lys Cys Thr Leu
  1               5                  10                  15

Leu Val Phe Gly Val Trp Ile Leu Tyr Ile Leu Lys Leu Asn Tyr Thr
                 20                  25                  30

Thr Glu Glu Cys Asp Met Lys Lys Met His Tyr Val Asp Pro Asp Arg
             35                  40                  45

Val Lys Arg Ala Gln Lys Tyr Ala Gln Gln Val Leu Gln Lys Glu Cys
         50                  55                  60

Arg Pro Lys Phe Ala Lys Thr Ser Met Ala Leu Leu Phe Glu His Arg
 65                  70                  75                  80

Tyr Ser Val Asp Leu Leu Pro Phe Val Gln Lys Ala Pro Lys Asp Ser
                 85                  90                  95

Glu Ala Glu Ser Lys Tyr Asp Pro Pro Phe Gly Phe Arg Lys Phe Ser
            100                 105                 110

Ser Lys Val Gln Thr Leu Leu Glu Leu Leu Pro Glu His Asp Leu Pro
        115                 120                 125

Glu His Leu Lys Ala Lys Thr Cys Arg Arg Cys Val Val Ile Gly Ser
    130                 135                 140

Gly Gly Ile Leu His Gly Leu Glu Leu Gly His Thr Leu Asn Gln Phe
145                 150                 155                 160

Asp Val Val Ile Arg Leu Asn Ser Ala Pro Val Glu Gly Tyr Ser Glu
                165                 170                 175
```

```
His Val Gly Asn Lys Thr Thr Ile Arg Met Thr Tyr Pro Glu Gly Ala
            180                 185                 190

Pro Leu Ser Asp Leu Glu Tyr Tyr Ser Asn Asp Leu Phe Val Ala Val
        195                 200                 205

Leu Phe Lys Ser Val Asp Phe Asn Trp Leu Gln Ala Met Val Lys Lys
        210                 215                 220

Glu Thr Leu Pro Phe Trp Val Arg Leu Phe Trp Lys Gln Val Ala
225                 230                 235                 240

Glu Lys Ile Pro Leu Gln Pro Lys His Phe Arg Ile Leu Asn Pro Val
            245                 250                 255

Ile Ile Lys Glu Thr Ala Phe Asp Ile Leu Gln Tyr Ser Glu Pro Gln
            260                 265                 270

Ser Arg Phe Trp Gly Arg Asp Lys Asn Val Pro Thr Ile Gly Val Ile
        275                 280                 285

Ala Val Val Leu Ala Thr His Leu Cys Asp Glu Val Ser Leu Ala Gly
        290                 295                 300

Phe Gly Tyr Asp Leu Asn Gln Pro Arg Thr Pro Leu His Tyr Phe Asp
305                 310                 315                 320

Ser Gln Cys Met Ala Ala Met Asn Phe Gln Thr Met His Asn Val Thr
            325                 330                 335

Thr Glu Thr Lys Phe Leu Leu Lys Leu Val Lys Glu Gly Val Val Lys
            340                 345                 350

Asp Leu Ser Gly Gly Ile Asp Arg Glu Phe
            355                 360

<210> SEQ ID NO 9
<211> LENGTH: 17
<212> TYPE: DNA
<213> ORGANISM: Artificial Sequence
<220> FEATURE:
<223> OTHER INFORMATION: Synthetic DNA

<400> SEQUENCE: 9
atgaaaaaaa tgcatta                                                17

<210> SEQ ID NO 10
<211> LENGTH: 17
<212> TYPE: DNA
<213> ORGANISM: Artificial Sequence
<220> FEATURE:
<223> OTHER INFORMATION: Synthetic DNA

<400> SEQUENCE: 10
tcaaaattca cgatcaa                                                17

<210> SEQ ID NO 11
<211> LENGTH: 48
<212> TYPE: PRT
<213> ORGANISM: Homo sapiens

<400> SEQUENCE: 11

Cys Arg Arg Cys Val Val Ile Gly Ser Gly Gly Ile Leu His Gly Leu
  1               5                  10                  15

Glu Leu Gly His Thr Leu Asn Gln Phe Asp Val Val Ile Arg Leu Asn
            20                  25                  30

Ser Ala Pro Val Gln Gly Tyr Ser Glu His Val Gly Asn Lys Thr Thr
        35                  40                  45
```

-continued

```
<210> SEQ ID NO 12
<211> LENGTH: 23
<212> TYPE: PRT
<213> ORGANISM: Homo sapiens

<400> SEQUENCE: 12

Pro Thr Ile Gly Val Ile Ala Val Val Leu Ala Thr His Leu Cys Asp
  1               5                  10                  15

Glu Val Ser Leu Ala Gly Phe
             20
```

SIALYLTRANSFERASE AND DNA ENCODING THE SAME

CROSS-REFERENCE TO RELATED APPLICATION

This is a continuation-in-part of U.S. Ser. No. 09/112,563 filed July 9, 1998 now abandoned.

BACKGROUND OF THE INVENTION

The present invention relates to a sialyltransferase and to a DNA encoding the same. More particularly, the present invention relates to an enzyme which synthesizes ganglioside $G_{M3}$ by transferring sialic acid to a galactose residue of lactosylceramide and to a DNA encoding the enzyme.

Human myelogenous leukemia cell line EL-60, which is a cell line that has acquired the ability of infinite proliferation as a result of tumorigenic transformation, is used generally and widely as a model for leukemia cells (Collins, S. J. Gallo, R. C., and Gallagher, R. E., Nature (London), 270, 347–349 (1977); Collins, S. J., Blood, 70, 1223 (1987)). The cell line does not differentiate even after continued cultivation and continues to proliferate while it remains as undifferentiated cells. However, when cultivation is continued with addition of phorbol ester, which is widely used as a differentiation inducer, the cell line stops the proliferation of cells and takes an appearance similar to that of monocytes or macrophages. This indicates that. differentiation has been induced. It has been reported that during this process, the amount of $G_{M3}$, which is a kind of ganglioside, increases considerably (Nojiri, E., Takaku, F., Tetsuka, T., and Saito, M., Blood, 64, 534–541(1984)), and when the ganglioside $G_{M3}$ is added exogenously, the cell line shows the same change as that observed with the addition of phorbol ester, i.e., the cells undergo monocytic differentiation (Saito, M., Terui, Y., and Nojiri, H., Biochem. Biophys. Res. Commun., 132, 223–231 (1985)). Also, it has been proved that in this differentiation process, $G_{M3}$ itself has an activity of inducing differentiation (Nojiri, H., Takaku, F., Miura, Y., and Saito, M., Proc. Natl. Acad. Sci. U.S.A., 83, 782–786 (1986)), and that chemically synthesized $G_{M3}$ also induces differentiation (Sugimoto, M. and Ogawa, T., Glycoconj. J., 2, 5–9 (1985); Saito, M., Nojiri, H., Ogino, H., Yuo, A., Ogura, H., Itoh, M., Tomita, K., Ogawa, T., Nagai, Y., and Kitagawa, S., FEBS Lett., 271, 85–88 (1990)).

On the other hand, it has been elucidated that sialic acid-containing glycolipids, in particular ganglioside, bear important functions in various biological phenomena and not only its functions but also its biosynthesis are being clarified. In vertebrates, many gangliosides (ganglio-series gangliosides) have a common precursor, $G_{M3}$, which has the simplest structure among major gangliosides and the $G_{M3}$ synthesis affords a basis for the biosynthesis of gangliosides which have major functions.

As described above, ganglioside $G_{M3}$ itself participates in the proliferation/differentiation of cells and tissues and it is suggested that the ganglioside $G_{M3}$ is a precursor for a group of higher gangliosides having various functions in vertebrates.

$G_{M3}$ has been considered to be synthesized from lactosylceramide by transfer of sialic acid to the galactose residue in lactosylceramide by CMP-sialic acid:lactosylceramide sialyltransferase (CMP-NeuAc: Gal$\beta$1-4Glc$\beta$1-1'Cer$\alpha$2,3-sialyltransferase; SAT-I). However, neither the transferase from mouse and human has been isolated nor the genes thereof have been identified.

Enzymes which transfer sialic acid through an $\alpha$2–3 ketoside bond are described in, for example, Wienstein et al., J. Biol. Chem., 257, 13835 (1982); Gillespie et al., Glycoconj., 7, 469 (1990); Gillespie, W., Kelm, S. and Paulson, J C., J. Biol. Chem., 267, p21001–21010 (1992); Lee, Y C., Kojima, N., Wada, E., Kurosawa, N., Nakaoka, T., Hashimoto, T. and Tsuji, S., J. Biol. Chem., 269, p10028–10033 (1994); Kim. Y J., Kim, K S., Kim, S H., Kim, C H., K o, J H., Choe, I S., Tsuji, S. and Lee, Y C., Biochem. Biophys. Res. Commun., 228, p324–327 (1996); and JP-A 5-336963. However, none of the enzymes is known to be involved in the synthesis of $G_{M3}$ or shows an enzyme activity of transferring sialic acid to lactosylceramide through an $\alpha$2–3 ketoside bond. Sandhoff, K. et al. presume that $\alpha$2–3 sialyltransferase (SAT4) is identical with the enzyme which synthesizes $G_{M3}$ (J. Biol. Chem., 268, 5341 (1993)). However, this is a presumption based on an indirect method, which fails to support that the enzymes are identical to each other as a substance.

In spite of various attempts which have been made in order to elucidate and control its biosynthesis according as the clarification of importance of ganglioside $G_{M3}$ proceeds, the above-mentioned sialyltransferase, which relates closely to the synthesis of $G_{M3}$, has not been isolated yet from mouse and human because of difficulty in preparing the enzyme protein and, hence, neither its gene expression control mechanism has been clarified yet nor its proteochemical or enzymological analysis has been performed successfully.

SUMMARY OF THE INVENTION

As a result of intensive investigation with view to elucidating the control mechanism of cell differentiation by carrying forward studies on gene expression control mechanism of and proteo-chemical and enzymological analyses of the above-mentioned sialyltransferase, the present inventors have-been successful in isolating cDNA having a nucleotide sequence encoding the sialyltransferase which participates in the above-mentioned $G_{M3}$ synthesis from mouse and human, by using an expression cloning method and based on the nucleotide-sequence, they have clarified the structure of the above-mentioned sialyltransferase. As a result, it revealed that the enzyme is low in homology with the known sialyltransferase and is believed to be a new enzyme, differing from the $\alpha$2–8 sialyltransferase, with which the identity was presumed by Sandhoff, K. supra.

Accordingly, the present invention provides a sialyltransferase having the following properties and a DNA having a nucleotide sequence encoding it.

(1) Activity:

The sialyltransferase transfers sialic acid from a sialic acid donor selectively to a 3-hydroxyl group of a galactose residue contained in lactosylceramide as a sialic acid acceptor to produce ganglioside $G_{M3}$.

(2) Optimal Reaction pH;

6.0 to 7.0.

(3) Activation:

The activity increases at least 1.5 times with 10 mm of $Mn^{2+}$ as compared with the case in the absence thereof.

Also, the present invention provides a sialyltransferase having the above-mentioned activity and having a C-terminal amino acid sequence shown by SEQ ID NO: 5 and a DNA encoding it as well as a sialyltransferase having the above-mentioned activity and having an amino acid sequence shown by SEQ ID NO: 6 or 11 and/or 12 and a DNA encoding it.

The sialic acid donor is preferably cytidine 5-monophosphsate-sialic acid (CMP-sialic acid).

The above-mentioned enzymes and DNAs are preferably those derived from a mammal, most preferably those derived from human.

The present invention also provides a sialyltransferase comprising the polypeptide (a) or the polypeptide (b) below and a DNA encoding it (a) A polypeptide having an amino sequence shown by SEQ ID NO: 2 or 8.

(b) A polypeptide having an amino acid sequence (a) above, which has therein substitution, deletion, insertion or rearrangement of one or a few amino acid residues, said sialyltransferase having an enzyme activity of transferring sialic acid from a sialic acid donor selectively to the 3-hydroxyl group of galactose residue contained in lactosylceramide as a sialic acid acceptor to produce ganglioside $G_{M3}$.

Specific examples of the DNA of the present invention include a DNA having a nucleotide sequence encoding all the amino acid sequence shown by SEQ ID NO: 2 or 8, or a DNA having partial sequences thereof, for example, DNA having a nucleotide sequence shown by SEQ ID NO: 1 or 7.

Further, the present invention provides a polypeptide comprising all or part of the polypeptide of sialyltransferase encoded by the nucleotide sequence of the above-mentioned DNA. From the polypeptide, a transmembrane domain may be deleted.

In addition, the present invention provides a recombinant vector comprising the DNA of the present invention; a transformant into which the DNA of the present invention is introduced, and in which the DNA can be expressed; and a method for producing a sialyltransferase or a polypeptide thereof, comprising cultivating the transformant as defined above in a suitable medium, to produce and accumulate in the culture the sialyltransferase or the polypeptide thereof encoded by the DNA, and collecting the sialyltransferase or the polypeptide thereof from the culture.

The phrase "encoding an enzyme" as used herein refers to encoding the polypeptide of the enzyme. Also, herein, the sialyltransferase of the present invention which has an enzyme activity of transferring sialic acid from a sialic acid donor selectively to the 3-hydroxyl group of the galactose residue contained in lactosylceramide as a sialic acid acceptor to form α2–3 linkage, thereby producing ganglioside $G_{M3}$, is also described as "sialyltransferase-1" or "SAT-I" for convenience's sake.

According to the present invention, a DNA of α2–3 sialyltransferase (SAT-I) which synthesize from lactosylceramide, ganglioside $G_{M3}$ that induces cell differentiation. According to the present invention, α2–3 sialyltransferase, i.e., $G_{M3}$ synthase, can be obtained easily by the use of the above-mentioned DNA.

Since the DNA encoding SAT-I is provided by the present invention, the elucidation of expression mechanism thereof will give an expectation for elucidation of the mechanism of cell differentiation.

BRIEF DESCRIPTION OF THE DRAWINGS

FIG. 2 is a diagram comparing the amino acid sequence of a sialylmotif (L and S) region of mouse SAT-I with a sialylmotif region of another sialyltransferase; the marks "*" under the sequences indicate common sequences appearing in the sialylmotif of other sialyltransferases, the marks "*" above the sequences indicate the part of mouse SAT-I that contains the amino acids identical with the amino acids in the common sequences of the sialylmotif, and the marks "-" above the sequences indicate the part that contains amino acids different from those in the common sequences of the sialylmotif.

FIG. 4 is a diagram comparing the amino acid sequence of a sialylmotif (L and S) region of human SAT-I with a sialylmotif region of another sialyltransferase.

DETAILED DESCRIPTION OF THE INVENTION

Figure 1:
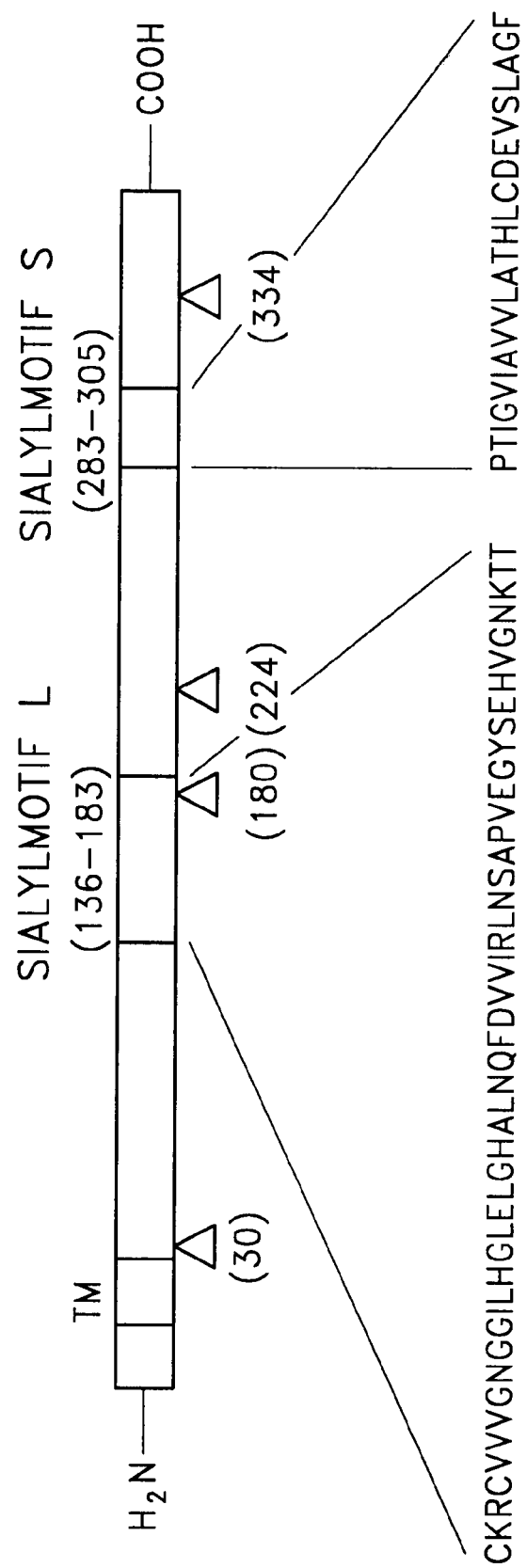
FIG. 1 is a schematic view showing the structure of mouse α2–3 sialyltransferase (SAT-I) of the present invention, in which Δ indicates an N-glycosylation site presumed from the amino acid sequence and TM indicates a transmembrane domain presumed from the amino acid sequence.

[1] Sialyltransferase-1 of the Present Invention (Enzyme of the Present Invention) and DNA Encoding the Same (DNA of the Present Invention)

The enzyme of the present invention includes sialyltransferases having the following activity:
(1) Activity:
The sialyltransferase selectively transfers sialic acid from a sialic acid donor to a 3-hydroxyl group of a galactose residue contained in lactosylceramide as a sialic acid acceptor, to produce ganglioside $G_{M3}$. In other words, the enzyme does not transfer substantially sialic acid to a position except for a 3-hydroxyl group of a galactose residue of the above-mentioned sialic acid acceptor. The sialic acid acceptor is preferably CMP-sialic acid.

Preferably, the enzyme of the present invention further has the following physico-chemical properties:
(2) Optimal Reaction pH:
This enzyme has high sialic acid transferring activity within the range of an enzyme reaction mixture pH of from 6.0 to 7.0 as measured by the enzyme activity assay method described in the examples below.
(3) Activation:
The activity of sialyltransferase increases at least 1.5 times in the presence of 10 mM of $Mn^{2+}$ as compared with the case in the absence thereof.

Further, the enzyme of the present invention includes sialyltransferases having an activity of transferring sialic acid to a 3-hydroxyl group of a galactose residue (preferably, the activity (1) above) and having a C-terminal amino acid sequence shown by SEQ ID NO; 5 as well as sialyltransferases having an activity of transferring sialic acid to a 3-hydroxyl group of a galactose residue (preferably, the activity (1) above) and having an amino acid sequence shown by SEQ ID NO: 6 or 11 and/or 12. The amino acid sequence shown by SEQ ID NO: 6 or 11 is a sequence which corresponds to a sialylmotif (sialylmotif L) existing in the sialyltransferase and which usually exists in the part corresponding to the amino acid numbers 136–183 in the amino acid sequence shown by SEQ ID NO: 2 or 8 in the amino acid sequence of the polypeptide of the sialyltransferase. The amino acid sequence shown by SEQ ID NO: 12 is a sequence which corresponds to another sialylmotif (sialylmotif S) existing in the sialyltransferase and which usually exists in the part corresponding to the amino acid numbers 283–305 in the amino acid sequence shown by SEQ ID NO: 2 or 8 in the amino acid sequence of the polypeptide of the sialyltransferase.

Specific examples of the polypeptide of the enzyme of the present invention includes those of amino acid numbers 38–359 or 1–359 in the amino acid sequence shown by SEQ ID NO: 2 and amino acid numbers 41–362 or 1–362 in the amino acid sequence shown by SEQ ID NO: 8.

The DNA of the present invention is not limited particularly as far as they encode those polypeptides and includes those encoding the polypeptides (a) or (b) below.

(a) A polypeptide having an amino sequence shown by SEQ ID NO: 2 or 8.

(b) A polypeptides having the amino acid sequence (a) above, which has therein substitution, deletion, insertion or rearrangement of one or a few amino acid residues and having an enzyme activity of transferring sialic acid to a 3-hydroxyl group of a galactose residue (preferably the activity (1) above).

In other words, the amino acid sequence shown by SEQ ID NO: 2 may have therein substitution, deletion, insertion or rearrangement of one or a few amino acid residues that do not substantially impair the activity of transferring sialic acid to a 3-hydroxyl group of a galactose residue (preferably the activity (1) above). The DNA of the present invention includes DNAs having any of substitution, deletion, insertion and rearrangement in their nucleotide sequence, encoding such polypeptides having therein any of substitution, deletion, insertion and rearrangement in their amino acid sequence. The term "a few amino acid residues" as used herein refers to the number of amino acids that may cause variations to the extent that the activity of the enzyme is not lost In the case of a polypeptide consisting of 360 amino acid residues, for example, it means about 20 or less, preferably about 10 or less. The activity of the enzyme can be measured without difficulty by a known method (JP-A 7-327678) by changing cDNA to be introduced into host cells and a substrate for the enzyme and since one skilled in the art can practice with ease, for example, by the method specifically described herein, the substitution, deletion, insertion or rearrangement of one or a few amino acid residues that does not substantially impart the target activity can be readily selected by using the presence or absence of the enzyme activity as an indicator. The substitution, deletion, insertion or rearrangement in the nucleotide sequence can be introduced into a DNA by synthesizing a sequence having a restriction enzyme-cleaved end on each terminal and containing both sides of the mutation point, i.e., substitution, deletion, insertion or rearrangement, followed by replacing this for the corresponding part of the nucleotide sequence of a non-mutated DNA Alternatively, site-specific mutagenesis (Kramer, W. and Frits, H. J., Meth. in Enzymol., 154, 350 (1987); Kunkel, T. A. et al., Meth. in Enzymol., 154, 367 (1987)) and the like can be used to introduce substitution, deletion, insertion or rearrangement into a DNA. Also, the DNA encoding a polypeptide having substitution, deletion, insertion or rearrangement of one or a few amino acid residues that does not substantially impair the activity in the amino acid sequence shown by SEQ ID NO: 2, may be obtained as a homologous or allelic variant.

The amino acid sequences shown by SEQ ID NO: 2 and SEQ ID NO: 8 are derived from mouse and human, respectively, it is predicted that there is a difference which does not affect the activity between individuals of each species. The substitution, deletion, insertion or rearrangement one or a few amino acid that does not substantially impair the activity is preferably within a range of mutation between individuals.

Specifically, the DNA of the present invention includes DNAs having nucleotide sequences encoding all the amino acid sequence shown by SEQ ID NO: 2 or 8, or DNAs having partial nucleotide sequences thereof. These DNAs are preferred but the present invention is not limited thereto. The term "DNAs having partial nucleotide sequences" as used herein refers to, for example, those DNAs which hybridize with DNA encoding a polypeptide of mouse or human sialyltransferase-1 (in particular, a part of amino acid numbers 30–362, 38–362, 41–362 or 136–183 in the amino acid sequence of SEQ ID NO: 8) so that they can be used as a probe for detecting the DNA of the sialyltransferase-1; which encode the polypeptides having an activity of the sialyltransferase-1; or which encode the polypeptides having antigenicity similar to that of the sialyltransferase-1, or DNAs or RNAs complementary thereto. The hybridization referred to above may be performed under stringent conditions by a method which is conventionally used for hybridizing DNA or RNA with DNA, such as screening. For example, the conditions used in screening DNA or the like include prehybridizing a target DNA in a solution containing 50% formamide, 5×SSPE (sodium chloride/sodium phosphate/EDTA buffer), 5×Denhardt's solution, 0.5% SDS, and 50 $\mu$g/ml of denatured salmon sperm DNA, adding to the solution $^{32}$P-labeled DNA of the present invention (for example, DNA having a nucleotide sequence shown by SEQ ID NO: 1 or 7), hybridizing it at 42°C. for 16 hours, and then washing it sequentially with 1×SSPE, 1% SDS, 0.1×SSPE, and 0.1% SDS at 550C. Although generally hybridization is performed mostly under the above-mentioned conditions, one skilled in the art can perform similar hybridization by changing the composition of each solution and conditions aiming at similar hybridization and, hence, the present invention is not limited to the above-described conditions as far as the conditions used enable one to obtain similar effects.

More specifically, the DNA of the present invention includes DNAs having the whole nucleotide sequence shown by SEQ ID NO; 1 or partial sequences thereof, which are preferred. Specific examples of these DNAs include a DNA having a nucleotide sequence of base numbers 202–1278 in the nucleotide sequence shown by SEQ ID NO: 1 or base numbers 278–1363, 365–1363, 389–1363 or 682–826 in the nucleotide sequence shown by SEQ ID NO: 7.

In the nucleotide sequence shown by SEQ ID NO: 1, the 5'-terminal portion of the open reading frame of cDNA of sialyltransferase-1 contains three in-frame ATG codons. The nucleotide sequences around the three ATG codons conserve each a purine base at the −3 position. This satisfies the Kozak's finding on efficient translation (Kozak, M., (1986) Cell, 44, 283–292) so that it is possible that any of the ATG codons functions as an initiation codon.

In the meantime, β-1,4-galactosyltransferase is known to contain two in-frame ATG codons (Nakazawa, K. et al. (1988) J. Biochem., 104, 165–168; Shaper, N. et al. (1988) J. Biol. Chem., 263, 10420–10428). Also, Shaper et al. showed that in the case of β-1,4-galactosyltransferase, translation starts at two sites, resulting in that the enzyme is synthesized in both longer and shorter forms. Further, Lopez et al. presented the evidence suggesting that the longer form preferentially targets membrane while the shorter form exists mainly in Golgi apparatus (Lopez, L. et al. (1991) J.

Biol. Chem., 266, 15984–15591). Similarly, in the case of the sialyltransferase, there is the possibility that plural ATG codons serve as an initiation codon. This is not certain yet. However, no matter how ATG codon may be an initiation codon, it is common that the polypeptide of the above-mentioned sialyltransferase-1 is encoded. Therefore, DNAs having nucleotide sequences starting with the second and third ATG codons, respectively are also embraced by the present invention. Specifically, the sialyltransferase-1 may have a region corresponding to amino acid numbers 41–359 in the amino acid sequence of SEQ ID NO: 2 or amino acid numbers 41–362 in the amino acid sequence of SEQ ID NO: 8.

From a single open reading frame starting with the first ATG codon in the sequence shown by SEQ ID NO: 1 is deduced a protein which consists of 359 amino acid residues, has a molecular weight of 41,244 Da, and contains four sites that can be an N-glycosylation site. From hydropathy plot prepared from this amino acid sequence, it can be seen that there exists in the sequence a 14 residue-long continuous, remarkably hydrophobic part ranging from the 16th to 29th amino acid residues counting from the N-terminal, which suggests that the protein has a transmembrane domain.

Figure 5:
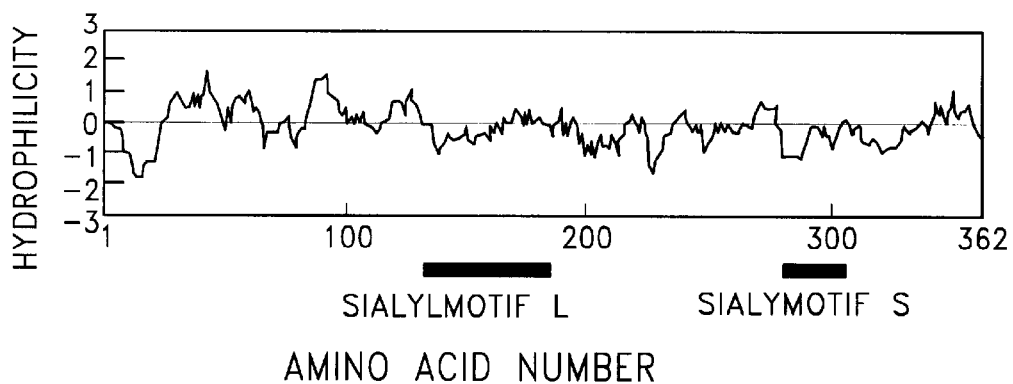
FIG. 5 is a graph illustrating hydropathy-plot of an amino acid sequence of human SAT-I deduced from a nucleotide sequence of the DNA of the present invention.
Figure 6A:
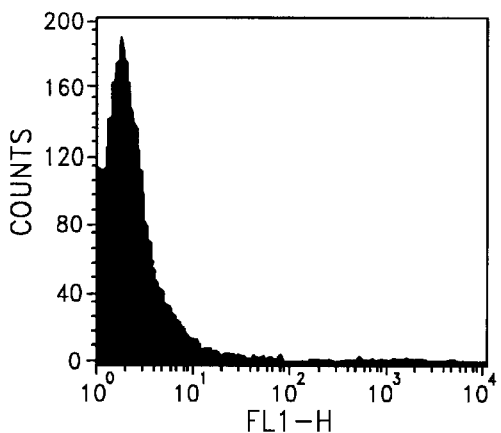
FIG. 6 is a graph showing results of flow analyses of ganglioside $G_{M3}$ expression in mouse lung carcinoma cells.
Figure 6B:
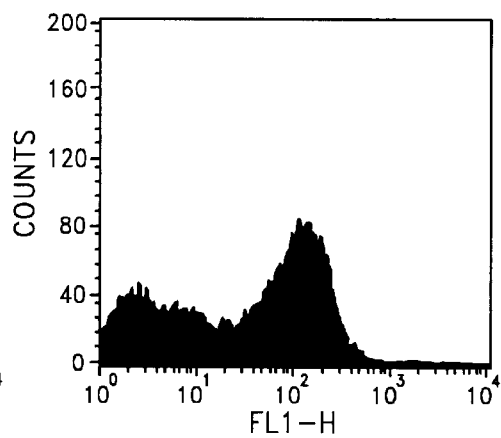
Figure 6C:
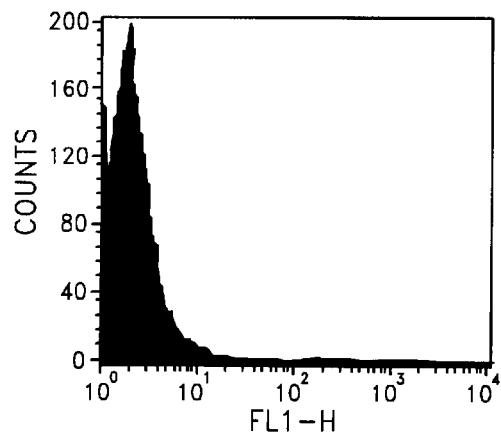
Figure 6D:
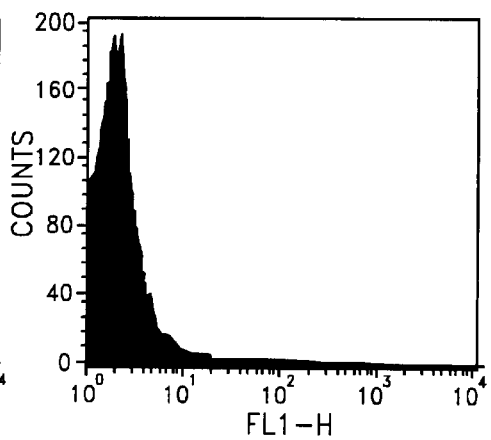

From a single open reading frame starting with the first ATG codon in the sequence shown by SEQ ID NO: 7 is deduced a protein which consists of 362 amino acid residues, has a molecular weight of 41,754 Da, and contains two sites that can be an N-glycosylation site. FIG. 5 is a graph illustrating hydropathy plot prepared from this amino acid sequence. From FIG. 5 it can be seen that there exists in the sequence a 14 residue-long continuous, remarkably hydrophobic part ranging from the 16th to 29th amino acid residues counting from the N-terminal, which suggests that the protein has a transmembrane domain.

It will be readily understood by one skilled in the art that the DNA of the present invention also includes DNAs having different nucleotide sequences by degeneracy of genetic codes.

Further, the DNA of the present invention include DNAs or RNAs complementary to the DNA of the present invention. Furthermore, the DNA of the present invention may be of a single strand of only a coding strand which encodes SAT-I or a double strand of the single strand and a DNA or RNA strand having a nucleotide sequence complementary thereto.

Also, the DNA of the present invention may have a nucleotide sequence over the whole encoding region which encodes the whole peptide of SAT-I or a nucleotide sequence encoding only a part of the polypeptide of SAT-I.

Now, generally, mammal sialyltransferases are known to have high homology in their amino acid sequence. The polypeptide which the DNA of the present invention encodes is expected to have a homology of about 65% or more in the species. The homology determined as a percentage of nucleotides which are identical to corresponding nucleotides in the coding region of SAT-I. Therefore, polypeptides having high homology with the polypeptides encoded by the DNAs of the present invention specifically disclosed herein and DNAs encoding such polypeptides (such as homologous or allelic variants) are also embraced by the present invention.

As described above, the polypeptide of SAT-I has a transmembrane domain. The part of the polypeptide of SAT-I that has lost the region starting from the N-terminal corresponding to the N-terminal inside the membrane and containing the region having the transmembrane domain is also embraced by the present invention. As far as such a polypeptide has an activity of SAT-I, the polypeptide is included in that contained in the enzyme of the present invention. Such a polypeptide includes, for example, an amino acid sequence of amino acids numbers 38 to 359 in the amino acid sequence shown by SEQ ID NO: 2, and amino acid numbers 30 to 362, 38 to 362 and 41 to 362 in the amino acid sequence shown by SEQ ID NO: 8.

[2] Method of Producing the DNA of the Invention

Hereafter, a method of producing the DNA of the present invention will be explained in detail. As the amino acid sequence of the polypeptide of SAT-I has been clarified by the present invention, it is possible to obtain the DNA by amplification from chromosomal DNA or m-RNA by a PCR method (polymerase chain reaction method) using an oligonucleotide primer prepared based on the amino acid sequence. Alternatively, the DNA of the present invention can also be produced by an expression cloning method, particularly the method which comprises the following steps.

(1) Cancer cells from mouse or human are treated with a differentiation inducing agent to cause differentiation.
(2) A cDNA library is prepared from differentiated cancer cells and is introduced into host cells.
(3) Host cells that have expressed ganglioside on the cell membrane are screened.
(4) The screened host cells are sorted to enrich the library.
(5) The introduced gene is excised from the enriched library.

The whole length of cDNA of the above-mentioned SAT-I is normally selected by means of screening.

Hereafter, an example of the method of producing the DNA of the present invention will be explained more specifically.

(1) Differentiation Induction in Cancer Cells

Cancer cells are preferably anchorage independent cells from mouse or human. Such cancer cells include blood cell lymphoma and leukemia cells, which are preferred. As such cells are preferred, for example, human-derived HL-60 (ATCC CCL-240), MOLT-4 (ATCC CRL-1582), and U937 (ATCC CRL-1593) and mouse-derived MI (ATCC TIB-192) and B-16 (ATCC CRL-6322) and fresh myelogenous leukemia cells can also be used. Among such cancer cells, most preferred are human-derived cells and HL-60 cells are particular preferred since differentiation induction is readily performed. Differentiation is induced by cultivating the cultivated cancer cell line for 20 hours or more, preferably for about 24 to 48 hours, after adding a differentiation inducing agent to the cancer cell line. Cultivation may be performed under conditions that are suited for the cells used. Usually, as general cell culture conditions, there can be used conditions of 5–7 vol % of $CO_2$ and 95–93 vol % of air at 37–38° C. As the differentiation inducing agent, there can be used, for example, phorbol ester (12-O-tetradecanoyl phorbol ester (TPA) etc.), dimethyl sulfoxide (DMSO), retinoic acid (RA), and $1\alpha,25$-dihydroxyvitamin $D_3$ ($1\alpha,25$ $(OH_2D_3)$) and the like. Although the present invention is not limited to the use of a particular one, preferred among them is TPA since it has relatively uniform differentiation inducing activity toward many leukemia cell lines. When HL-60 is used as a cancer cell and TPA is used as a differentiation inducing agent, 48 hour cultivation in the presence of TPA in an amount of about 24 nM leads to the differentiation of HL-60 into monocyte/macrophage like cells, showing morphological changes.

(2) Construction of cDNA from Differentiated Cancer Cells

1) Preparation of RNA from Differentiated Cancer Cells

The cancer cells of which differentiation is induced in above (1) are collected by centrifugation preferably at 500 to 2,000×g and total RNA is prepared from the cells by a known method, for example, a guanidine thiocyanate/CsCl method (Kingston, R. E., (1991) in Current Protocols in Molecular Biology, Suppl. 14, Unit 4.2, Green Publishing Associates and Wiley Interscience, New York). From the total RNA thus obtained is purified poly(A)$^+$RNA by oligo-(dT)cellulose column chromatography or the like.

2) Construction of cDNA from Poly(A)$^+$RNA

Reverse transcription PCR using the above-mentioned poly(A)$^+$RNA as a template and also an oligonucleotide primers allows amplification of cDNA derived from the cancer cells. PCR may be performed in the same manner as a conventional method. Specific method thereof may be as follows. Namely, a buffer solution (final volume 20 μl) containing 1 μl of poly(A)$^+$RNA, 100 pmol of oligo-(dT), 100 pmol each of random oligonucleotide primers, 500 μl each of 4 kinds of deoxyribonucleoside triphosphates, 200 units of M-MLV reverse transcriptase (Gibco BRL), 1 mM dithiothreitol (DTT), 120 units of RNase (ribonuclease) inhibitor (manufactured by TAKARA SHUZO CO., LTD.) was incubated at 50° C. for 60 minutes to synthesize a cDNA primary strand. Next, a reaction mixture (final volume 50 μl) containing 5 μl of the above-mentioned reverse transcriptase reaction mixture, 100 pmol each of random oligonucleotide primers, 250 μM each of 4 kinds of deoxyribonucleoside triphosphates, and 1.25 units of Taq polymerase was incubated by repeating 35 cycles of 95° C. for 1 minute, 46 to 62° C. for 1 minute, and 72° C. for 2 minutes.

The cDNA of cancer cells thus obtained is made to be held by an expression vector and introduced into host cells for screening the host cells. As the host cells, there can be used any cells as far as they are cells of a mammalian-derived cell line which are lactosylceramide-positive. Examples of such include human Namalwa cells (Hosoi et al.: Cytotechnology, 1, 151 (1988)), Chinese hamster-derived CHO cells (ATCC CCL61, etc.), monkey-derived COS cells (ATCC CRL1650, etc.), mouse-derived 3LL cells (Taniguchi, S., Shinshu University Aging Adaptation Research Center)) and so on. However, since the detection of SAT-I enzyme activity can be made easier in the present invention, those cultivated cells which are further $G_{M3}$-negative are preferred. Examples of such cells include 3LL-HK46 cell (Inokuchi, J., (Seikagaku Corporation)), a mutant of 3LL cell, which is preferred. The expression vector includes pCEV18 (Maruyama, K. (donated from Tokyo University, Medical Science Research Institute, now Tokyo Medical Dental University), pCXN2 (Niwa, H., Yamamura, K. and Miyazaki, J. (Gene, 108, p193–200 (1991)), PFLAG-CMV-2 (manufactured by Eastman Kodak), pAGE107 (Miyaji et al., Cytotechnology, 3, 133 (1990)), pAS3-3 (JP-A 2-227075), pAMoERC3Sc(JP-A 5-336963), pcD2 (Chen, C. et al., Mol. Cell. Biol., 7, 2745–2752 (1987)) and the like and can be selected appropriately taking into consideration the host cell to be used. For example, when 3LL-HK46 is used as a host cell, it is preferred that pCEV18 be used as an expression vector. Introduction, into a vector, of the PCR product prepared based on poly(A)$^+$RNA of a cancer cell as described above is performed by a method selected from known methods which is suited for the vector to be used.

3) Introduction of cDNA Library Into a Host Cell

The cDNA library constructed by the above-mentioned method is transfected to host cells by a known technique. Specifically, there can be cited, for example, an electroporation method (Miyaji, et al., Cytotechnology, 3, 133 (1990)), a calcium phosphate method (JP-A 2-227075), and a lipofection method (Philip, L. F. et al., Proc. Natl. Acad. Sci. USA, 84, 7413 (1987)), and selected suitably. However, the electroporation method is preferred. Human α2–8 sialyltransferase is an enzyme synthesizing $G_{D3}$ from $G_{D3}$, and a cell to which a DNA encoding the enzyme expresses $G_{D3}$ on its cell membrane. Detection of the $G_{D3}$ can be easily conducted. When cDNA encoding SAT-I is detected, therefore, it is also possible and preferable to transfect, in advance or simultaneously, to host cells, DNA encoding human α2–8 sialyltransferase (JP-A 7-327678, etc.), in order to more precisely detect the SAT-I activity. Such a pretransfection or simultaneous transfection is preferred. Therefore, when the cDNA library constructed by using pCEV18, for example, as a vector is introduced into 3LL-HK46 cells having no $G_{D3}$ synthesis pathway as a host cell, pCEV18 holding the cDNA library may be transfected to normal 3LL-HK46 cells directly or simultaneously with the vector into which the cDNA of α2–8 sialyltransferase has been introduced. Also, 3LL-ST28 cells originally expressing α2–8 sialyltransferase may be transfected with an eukaryote expression vector such as pCEV18, containing cDNA of the above-mentioned library. The 3LL-ST28 cells is produced by introducing cDNA of α2–8 sialyltransferase to 3LL-HK46 cells by using pCEV18.

(3) Detection of Host Cells Expressing Ganglioside

Host cells into which cDNA library has been introduced are cultivated under generally used cell culture conditions. After at least 24 hours, preferably after 36 to 48 hours, from the introduction of cDNA, the host cells are stained by immuno-staining using an anti-ganglioside antibody or a lectin which bonds to ganglioside. The staining method using antibodies is more accurate and preferred. For example, when 3LL-HK46 cell is used as a host cell, the expressing cells are detected by using an antibody which recognizes $G_{M3}$ that has been expressed on the cell membrane, for example, anti-$G_{M3}$ monoclonal antibody M2590 (the monoclonal antibody which L612 (ATCC CRL10724)) produces: J. Biol. Chem., 260, 13328–13333 (1985)). The immuno-staining can be performed by a conventional method. When the above-mentioned 3LL-ST28 is used as a host cell, for example, $G_{D3}$, produced upon the introduction of the DNA of the present invention is detected. Immuno-staining for detecting $G_{D3}$ may be performed by a conventional method generally used (JP-A 2-327678). In this case, the primary antibody to be used is not limited particularly as far as it is an antibody which recognizes $G_{D3}$ However, monoclonal antibodies are preferred and examples of which include anti-$G_{D3}$ monoclonal antibody R24 (monoclonal antibody which a hybridoma (ATCC HB8445) produces: Cancer Res., 49, p191–196 (1989)), which is preferred. Specifically, the immuno-staining method using the above-mentioned generally employed antibodies is mentioned. Namely, the host cells (1×10$^5$ cells) after the above-mentioned cultivation are washed about 2 or 3 times by centrifugation in a BSA solution (0.1% BSA PBS(+)) and the cells are suspended in 100 μl of the BSA solution containing the primary antibody. After allowing the suspension to react under ice cooling for 30 minutes, the cells are washed with the above-mentioned BSA solution 2 times or so. Further, in 100 μl of a BSA solution containing 1 μl of FITC-labeled secondary antibody against the primary antibody, the cells are left to stand for 30 minutes under ice cooling for reaction. The cells are washed with a BSA solution once and those cells which show strong fluorescence are detected by using a flow cytometer (FACScalibur:

manufactured by Becton Dickinson). Cells showing strong fluorescence, for example, 5% of the total cells, are selected by a cell sorter and plasmid DNA is extracted therefrom. The extraction of plasmid DNA from the host cells is performed by a conventional method.

(4) Sorting of SAT-I cDNA and Obtaining of cDNA

The plasmid DNA obtained by the above-described operation is transfected to a suitable host cell line and the procedure of immuno-staining with the anti-$G_{M3}$ antibody and recovery of strong fluorescence-showing cells in an amount of 5% of the total cells by using a flow cytometer, for example, is repeated twice or more to enrich the target cDNA by sorting. The host cell used for the sorting is preferably cultivated mammalian cells, of which 3LL-HK46 is particularly preferred. The vector to be used is not limited particularly and any expression vectors for mammalian cells may be used, but pCEV18 is preferred. The above-mentioned vector holding the target cDNA enriched by sorting is transfected to mammalian-derived cultivated cells lacking $G_{D3}$ synthesis pathway, such as 3LL-HK46, simultaneously with the expression vector made by introducing a human α2–8 sialyltransferase cDNA into an expression vector for mammalian cells, such as pBKCMV (manufactured by STRATAGENE CO.) and detection by immuno-staining and a flow cytometer is conducted in the same manner as described above to obtain cells that show strong fluorescence in an amount of 5% of the total cells. From these cells is extracted plasmid DNA by a conventional method. The cDNA excised by a conventional method from the plasmid DNA is used to transform E. coli DH10B (manufactured by GIBCO CO.) therewith, and the transfected E. coli cells are inoculated so that 100 colonies per well can be formed, followed by sib selection to finally obtain a clone containing an insert of about 2 kbp.

(5) Determination of the Nucleotide Sequence of cDNA Encoding SAT-I

The nucleotide sequence of the cDNA obtained as described above, as is or after subcloning in a suitable plasmid such as pCRII, is determined by a conventional method.

The nucleotide sequence of the mouse SAT-I-encoding cDNA determined as described above and amino acid sequence deduced from the nucleotide sequence are shown by SEQ ID NO: 1 and the amino acid sequence alone is shown by SEQ ID NO: 2.

The nucleotide sequence of the human SAT-I-encoding cDNA determined as described above and amino acid sequence deduced from the nucleotide sequence are shown by SEQ ID NO: 7 and the amino acid sequence alone is shown by SEQ ID NO: 8.

Further, the DNA encoding the polypeptide of SAT-I which lacks a transmembrane domain, i.e., which is in the form of solubilized protein can be obtained as follows. Namely, based on the nucleotide sequence shown by SEQ ID NO: 1 or 7 is prepared a primer selected to have a truncated form at the N-terminal side of the polypeptide of the enzyme, and the target DNA is amplified by a PCR method using the cDNA of cloned SAT-I as a template. For example, when a DNA encoding the polypeptide of a truncated form that lacks 37 amino acid residues at the N-terminal is to be obtained, an oligonucleotide primer is synthesized based on the nucleotide sequence existing at the 3'- and 5'-terminals of the target nucleotide sequence, for example. An oligonucleotide primers having nucleotide sequences are shown by SEQ ID NO: 3 and SEQ ID NO: 4 for the nucleotide sequence shown by SEQ ID NO: 1, SEQ ID NO: 9 and SEQ ID NO: 10 for the nucleotide sequence shown by SEQ ID NO: 7, respectively, for example, may be used as 5'- and 3'- primers, respectively, in order to perform PCR. Then, the target DNA can be obtained from the amplified PCR product, after purification, if desired.

[3] SAT-I Polypeptide Encoded by the Nucleotide Sequence of the DNA of the Present Invention The present invention provides SAT-I polypeptide encoded by the DNA of the present invention. The polypeptide may be single or fused with one or more other polypeptides. The polypeptide may also lack a transmnembrane domain.

The polypeptide may be with or without a sugar chain. The kind of sugar chain is not limited particularly.

Such a polypeptide can be obtained by, for example, the production method as described below. Determination of presence or absence of the above-mentioned activity or function can be practiced by changing the cDNA to be introduced into host cells and the substrate for the enzyme in the assay of enzyme activity as described in JP-A 7-327678 and can be performed with ease by one skilled in the art based on, for example, the method described herein specifically.

[4] Production Method for SAT-I or Polypeptide Thereof Utilizing the DNA of the Present Invention The SAT-I or the polypeptide thereof can be produced by cultivating cells transformed with the above-mentioned DNA of the present invention in a suitable medium, to produce and accumulate in the culture the SAT-I or the polypeptide thereof encoded by the DNA of the present invention, and collecting the SAT-I or the polypeptide thereof from the culture.

The cells transformed with the DNA of the present invention can be obtained by inserting a fragment of the DNA of the present invention into a known expression vector to construct a recombinant plasmid and conducting transformation with the recombinant plasmid. The present invention also provides a recombinant vector, that is, a recombinant plasmid comprising the DNA of the present invention; a transformant into which the DNA of the present invention is introduced, and in which the DNA can be expressed (for example, a transformant comprising the recombinant vector) which can be used for production of the enzyme of the present invention.

Examples of the cells which can be used include prokaryotic cells such as E. coli and eukaryotic cells such as mammalian cells. When prokaryotic cells such as E. coli are used, there occurs no addition of sugar chain to the SAT-I polypeptide to be produced by the expression of the DNA of the present invention and, hence, pure SAT-I polypeptide can be obtained. On the other hand, when eukaryotic cells such as mammalian cells are used, addition of sugar chain(s) to the SAT-I polypeptide produced by the expression of the DNA of the present invention occurs. Therefore, polypeptides can be obtained in the same form as ordinary SAT-I which contains also a sugar chain.

In this production method, a host-vector-system usually used in the production of proteins may be used. While it is preferred to use a combination of mammalian-derived cultivated cell, such as 3LL-HK46 cell, 3LL-ST28 cell or COS-1 cell, and an expression vector for mammalian cells, such as pCEV18, pME18S (Maruyama et al., Med. Immunol., 20, 27 (1990)), the present invention is not limited thereto The medium and cultivation conditions may be selected suitably depending on the host cell to be used.

While the DNA of the present invention may be expressed over the whole length thereof, it may be expressed as a fused polypeptide with another polypeptide. Also, a part of the DNA of the present invention may be expressed as a partial polypeptide.

A specific example of construction of recombinant plasmid which expresses the above-mentioned fused polypeptide is by the following method. Namely, the DNA of the present invention is incorporated into a vector constructed so that a gene introduced into a plasmid such as pGIR201protA (Kitagawa, H. and Paulson, J. C., J. Biol. Chem., 269, 1394–1401(1994)) can be expressed as a fused protein by a conventional method to construct a vector having genes for plural proteins on the same reading frame. Then, from the vector is excised NheI fragment, which encodes a fused protein, and the fragment is ligated to a suitable vector such as pCEV18 by the same operation as described above.

The SAT-I or the polypeptide thereof of the present invention can be collected from the culture by a known purification method for polypeptides. Specifically, there can be used affinity chromatography using a Sepharose column to which lactosylceramide or CMP-sialic acid, for example is bonded. When the DNA of the present invention is expressed as a fused polypeptide, the culture of the host cell can be subjected to affinity chromatography using a column to which a substance is bonded having high affinity for the polypeptide fused with SAT-I, such as antibody, thereby purifying the fused polypeptide. A linker having an amino acid sequence which a specified proteolytic enzyme can recognize and cleave may be incorporated in advance between the SAT-I and the other polypeptide in the fused polypeptide. This allows the cleavage to occur at the linker site of the fused polypeptide after purification thereof so that SAT-I. The combination of the specified proteolytic enzyme and the specified sequence which the enzyme recognizes is, for example, a combination of signal peptidase which acts upon the synthesis of proinsulin and signal peptide of insulin. The above-mentioned culture includes a medium and cells in the medium.

The activity of sialyltransferase can be assayed by changing the substrate for the enzyme in a conventional assay method for assaying general ganglioside synthesis (JP-A 7-327678). For example, a suitable amount of the culture or the enzyme purified by the above-described method is added to a reaction mixture containing 100 mM sodium cacodylate, 10 mM manganese chloride, 0.2 mM CMP-radioactive substance-labeled sialic acid, 0.4 mM lactosylceramide, and 0.3% Triton CF-54. The mixture is adjusted to pH 6.5 and incubated at 37° C. for 2 hours and the reaction product is developed by a conventional thin layer chromatography and the enzyme activity is determined by using Fujix BAS2000 Bio Imaging Analyzer (manufactured by Fuji Photo Film Co., Ltd.).

EXAMPLES

The present invention will be described in further detail by examples. However, the present invention is not limited thereto without exceeding the object of the present invention.

Example 1

(1) Differentiation Induction of B-16 Cell and Construction of cDNA

Mouse melanoma B-16 cells were cultivated in RPMI-1640 (manufactured by NISSUI PRARM. CO.) containing 24 nM TPA under the conditions of 5 vol % $CO_2$ and 95 vol % air at 37°C. for 48 hours to induce differentiation. The cultivated cells were collected by centrifugation at 1000×g and total RNA was prepared from the collected cells by guanidine thiocyanate-acid-phenol-chloroform method (AGPC method). From differentiated $5×10^6$ cells was obtained about 40 Mg of RNA. From the RNA, poly(A)$^+$ RNA was purified by oligo-(dT) cellulose column chromatography.

The poly(A)$^+$RNA was used as a template for reverse transcription reaction to construct a primary strand of DNA, and the DNA in turn was used for synthesizing double-stranded cDNA (Gubber, V. and Hoffman, B. J., Gene, 25, 283 (1983)).

To the double-stranded cDNA was ligated a restriction enzyme BSTX1 adapter and the ligate was introduced into the BSTX1 site of pCEV18 to construct a cDNA library.

(2) Transfection of cDNA to 3LL-HK46 cells

The above-mentioned cDNA library was introduced into 3LL-HK46 cells by using an electroporation method and the transfected cells were cultivated for 48 hours under the conditions of 5 vol % $CO_2$ and 95 vol % air at 37° C.

(3) Detection of Host Cells Expressing Ganglioside and Preparation of cDNA

The 3LL-HK46 cells after the cultivation were immuno-stained with M2590, anti-$G_{M3}$ antibody, and with FITC-labeled rabbit anti-murine IgG antibody. The stained cells were passed through a flow cytometer (FACScalibur) to detect fluorescence-positive cells. 5% of the cells on the positive side were collected and plasmid DNA was prepared therefrom. Then, the procedures of introduction of cDNA into 3LL-HK46 cells by electroporation, 48-hour cultivation of the transfected cells, immuno-staining, and detection and collection by using a flow cytometer were further repeated twice.

The plasmids finally obtained by this method were introduced into 3LL-HK46 cells together with pBKCMV $G_{D3}$ (a plasmid obtained by introducing the cDNA of human α2–8 sialyltransferase ($G_{D3}$ synthase) to pBKCMV plasmid vector manufactured by STRATAGENE CO.). After cultivating them for 48 hours, the resulting cells were immuno-stained with R24, anti-$G_{D3}$ antibody, and with FITC-labeled rabbit anti-murine IgG antibody, and 5% of the total cells which show strong fluorescence were detected by a flow cytometer and collected.

From these cells was prepared plasmid DNA, which then was transfected to *E. coli* DH10B (manufactured by GIBCO) by electroporation. After repeating the transfection and screening with ampicillin twice, positive colonies were dispensed to each well in a 96-well microplate in an amount of 100 colonies per well. Nine (9) microplates were inoculated with the transfected cells and only one well was selected by sib selection. Then, 2,400 colonies derived from this single well were extended to twenty five (25) 96-well microplates in a population of 1 colony per well and further sib selection gave rise to a positive clone (pCEVmS1) The pCEVmS1 thus obtained was expressed in 3LL-HK46 cells temporarily and flow cytometry analysis was performed using anti-$G_{M3}$ antibody (M2590) in the same manner as described above. 3LL-HK46 cells temporarily expressing pCEV18, as a control, did not express $G_{M3}$ on the cell membrane whereas 3LL-HK46 cells temporarily expressing pCEVmS1 expressed $G_{M3}$ on the cell membrane and fluorescence was detected.

(4) Determination of Nucleotide Sequence

The nucleotide sequence of double-stranded DNA of pCEVmsl was determined by a dideoxy chain termination method using an autocycle sequencing kit (manufactured by PHARMACIA CO.) and Pharmacia A.L.F. DNA sequencer (manufactured by PHARMACIA CO.). The nucleotide sequence thus determined and an amino acid sequence deduced therefrom are shown by SEQ ID NO: 1 and the amino acid sequence alone is shown by SEQ ID NO:2. The cDNA insert mS1 which is contained in pCEVmS1 is of about 2.1 kbp and is revealed to encode a protein (molecular weight 41,244 Da containing 359 amino acid residues starting with a nucleotide at 202 position as a translation initiation point. FIG. 1 is a schematic view which illustrates the structure expected from the amino acid sequence. As a result of hydropathy plot analysis, the amino acid sequence was revealed to correspond to a type-2 membrane protein in which the transmembrane domain (TM in FIG. 1) exists in the region of the 16th to 29th amino acid residues on the N-terminals. Search of this sequence with gene data base in GenBank showed no high homology with any of the data therein. However, with regard to the sialylmotifs (L and S) in the sialyltransferase homologous region existing in the central part and C-terminal region of the sequence for sialyltransferase, relatively high homology was recognized although some substitution was observed (FIG. 2). The sialyltransferases used for comparison were eleven (11) species, i.e., h2,3ST (JP-A 5-336963), rSTX (J. Biol. Chem., 268, 11504–11507 (1993)), rST3N-1 (J. Biol. Chem., 267, 21011–21019 (1992)), hST3N-2 (J. Biol. Chem., 268, 22782–22787 (1993)), pST3O-1 (J. Biol. Chem., 276, 21004–21010 (1992)), mST3O-2 (Eur. J. Biochem., 216, 377–385 (1993)), mST4' (NCBI Seq. ID 558532), hSAT4(a) (Gycbiology, 5, 319–325 (1995)), hST6N (Nuc. Acids Res., 18, 667 (1990)), rST6N (J. Biol. Chem., 262, 17735–17743 (1987)), h2,8ST (JP-A 7-327678). The results suggest that SAT-I which is encoded by the insert mS1 in pCEVmS1 belongs to the sialyltransferase family. Further, the amino acid sequence indicates existence of four consensus sequences of the N-glycosylation site (Δ in FIG. 1), whereas the two sites thereof on the N-terminal side exist near the transmembrane domain and in the sialylmotifs so that these two N-terminal side sites could be less N-glycosylated as compared with the two sites on the C-terminal side.

(5) $G_{M3}$ Synthesis in Cells Expressing SAT-I cDNA pCEVmS1 obtained by incorporating the above-mentioned SAT-I-encoding cDNA (mSAT-I cDNA) into expression vector pCEV18 was transfected to 3LL-HK46 cells by an electroporation method and the $G_{M3}$ synthase activity of the cells after 48-hour cultivation was assayed by the following method. Namely, 20 μl of a reaction mixture (pH 6.5) containing 0.1 mM CMP-($^{14}$C)-sialic acid ($2\times10^3$ CPM), 0.4 mM lactosylceramide, 0.3% (W/V) Triton CF-54, 10 mM $MgCl_2$, 100 mM sodium cacodylate, 150 μg of the homogenate of 3LL-HK46 cells to which pCEVmS1 was incorporated, and 1 mM sialidase inhibitor (2,3-dehydro-2-deoxy-N-acetylsialic acid (2,3-dehydro-2-deoxy-NeuAc, manufactured by BOEHRINGER MANNHEIM GMBH) was incubated at 37° C. for 2 hours and then 10 μl of methanol was added thereto to stop the reaction. 8 μl of the reaction mixture was charged on a C18 reversed phase thin layer chromatography plate (RP-18W HPTLC plate, manufactured by MERCK CO.) and developed with water for 10 minutes. Radioactive substance-labeled reaction products were scrubbed from the original point and $G_{M3}$ was collected therefrom by extraction with 300 μl of chloroform/methanol (1:1, V/V). After the extracts were concentrated to dryness, they were charged on a 60HPTLC plate (manufactured by MERCK CO.) for silica gel thin layer chromatography. After development with chloroform/methanol/0.5% aqueous $CaCl_2$ solution (55:45:10:, V/V/V), the layer was treated with orcinol sulfate to develop color and measured of radioactivity incorporated into ganglioside using Fujix BAS2000 Bio Imaging Analyzer (manufactured by FUJI PHOTO FILM CO., LTD.). The results revealed uptake of $^-$C by ganglioside $G_{M3}$ and $G_{M3}$ synthesis by SAT-I was detected in the SAT-I cDNA-transfected cells.

The $G_{M3}$ synthase activity was high at pH 6.0 to 7.0, particularly at around pH 6.5 and increased at least 1.5 times in the presence of 10 mM of $Mn^{2+}$.

Example 2

(1) Differentiation Induction of HL-60 Cell and Construction of cDNA

HL-60 cells ($2\times10^5$ to $3\times10^5$ cells/ml) were cultivated in RPMI-1640 (manufactured by NISSUI PHARM. CO.) containing 24 nM TPA and 10% fetal calf serum under the conditions of 5 vol % $CO_2$ and 95 vol % air at 37° C. for 48 hours to induce differentiation. From the cells, poly(A)$^+$ RNA was isolated using a Fast Track mRNA isolation kit (Invitrogen).

The poly(A)$^+$RNA was used as a template for reverse transcription reaction to construct a primary strand of DNA, and the DNA in turn was used for synthesizing double-stranded cDNA (Gubber, V. and Hoffman, B. J., Gene, 25, 283 (1983)).

To the double-stranded cDNA was ligated a restriction enzyme BSTX1 adapter and the ligate was introduced into the BSTX1 site of pCEV18 to construct a cDNA library. The cDNA library was divided into eight parts, and each part was amplified separately in *Escherichia coli* DH10B (Life Technologies, Inc.). The amplified cDNA was purified with Qiagen Tip (Qiagen).

(2) Transfection of cDNA to 3LL-HK46 Cells

The above-mentioned cDNA library (100 μg of the plasmid DNA) was introduced into $5\times10^6$ 3LL-HK46 cells by using an electroporation method (180 V, 600 μF) and the transfected cells were cultivated for 48 hours under the conditions of 5 vol % $CO_2$ and 95 vol % air at 37° C.

(3) Detection of Host Cells Expressing Ganglioside and Preparation of cDNA

The 3LL-HK46 cells after the cultivation were collected and washed with PBS(−). Then, the cells were reacted with anti-$G_{M3}$ antibody M2590 for 30 min on ice, and immuno-stained with FITC-conjugated rabbit anti-mouse IgG monoclonal antibody for 30 min on ice. The stained cells were passed through a flow cytometer (FACScalibur) to detect fluorescence-positive cells 5% of the cells on the positive side were collected with an EPICS Elite ESP cell sorter (Coulter), and plasmid DNA was prepared therefrom. Then, the procedures of introduction of cDNA into 3LL-HK46 cells by electroporation, 48-hour cultivation of the transfected cells, itmnuno-staining, and detection and collection by using a flow cytometer were further repeated twice.

The plasmids finally obtained by this method were introduced into $5\times10^6$ 3LL-HK46 cells together with pBKCMV $G_{D3}$ (a plasmid obtained by introducing the cDNA of human α2–8 sialyltransferase ($G_{D3}$ synthase) to pBKCMV plasmid vector manufactured by STRATAGENE CO.). After cultivating them for 48 hours, the resulting cells were immuno-stained with anti-$G_{D3}$ antibody R24, and with FITC-conjugated rabbit anti-mouse IgG antibody. Cells which show strong fluorescence were detected by a flow cytometer and 0.6% of the cells on the strong fluorescent side were collected with a FACS Vantage cell sorter (Becton Dickinson).

From these cells was prepared plasmid DNA, which then was transfected to *E. coli* DH10B by electroporation. After repeating the transfection and screening with ampicillin twice, positive colonies were dispensed to each well in a 96-well microplate in an amount of 100 colonies per well. Nine (9) microplates were inoculated with the transfected cells and only one well was selected by sib selection. Then, 2,400 colonies derived from this single well were extended to twenty five (25) 96-well microplates in a population of 1 colony per well and further sib selection gave rise to a positive clone (pCEV4C7).

In particular, when 3LL-ST28 cells were used as a host cell, not less than 3 times fluorescence intensity was obtained compared with a case in which 3LL-HK46 cells were co-transfected with a plasmid DNA comprising the DNA of the present invention and pBKCMVGD3. Therefore, in the above-mentioned sib selection, co-transfection was not used and 3LL-ST28 cells were used as a host cell.

(4) Determination of Nucleotide Sequence

Figure 3:
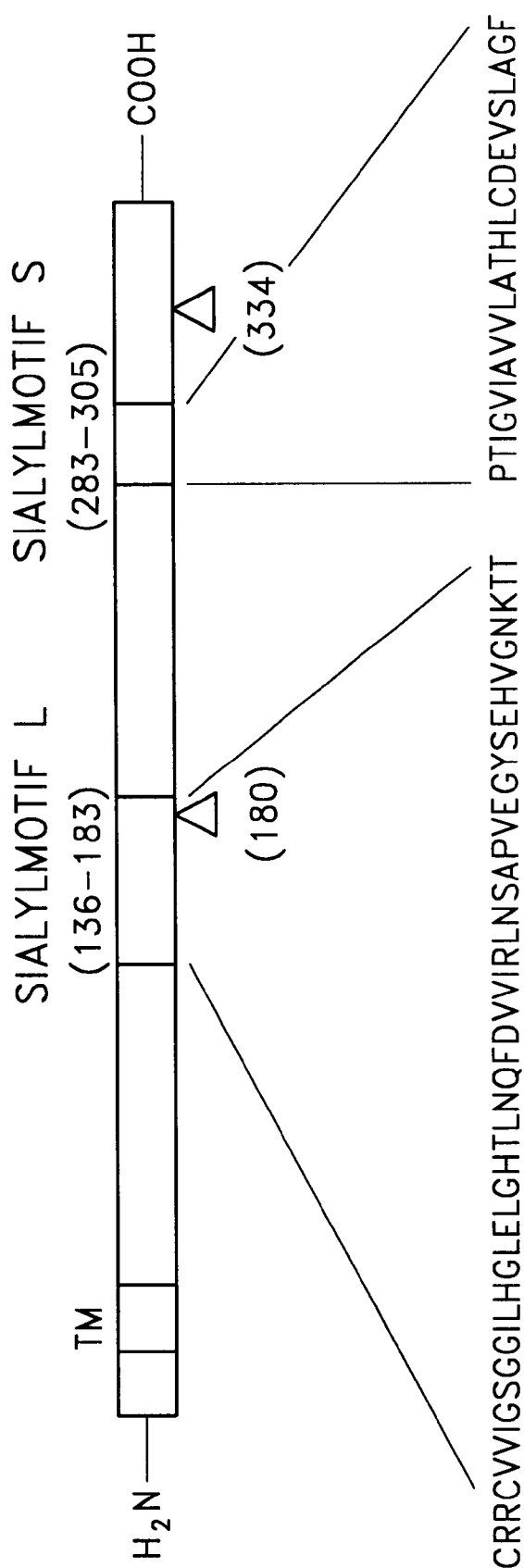
FIG. 3 is a schematic view showing the structure of human α2–3 sialyltransferase (SAT-I) of the present invention, in which Δ indicates an N-glycosylation site presumed from the amino acid sequence and TM indicates a transmembrane domain presumed from the amino acid sequence.

The nucleotide sequence of double-stranded DNA of pCEV4C7 was determined by a dideoxy chain termination method using an autocycle sequencing kit (manufactured by PHARMACIA CO.) and Pharmacia A.L.F. DNA sequencer (manufactured by PHARMACIA CO.). The nucleotide sequence thus determined and an amino acid sequence deduced therefrom are shown by SEQ ID NO: 7 and the amino acid sequence alone is shown by SEQ ID NO: 8. The cDNA insert 4C7 which is contained in pCEV4C7 is of about 2,359 bp and is revealed to encode a protein (molecular weight 41,754 Da containing 362 amino acid residues starting with a nucleotide at 278 position as a translation initiation point. FIG. 3 is a schematic view which illustrates the structure expected from the amino acid sequence. As a result of hydropathy plot analysis, the amino acid sequence was revealed to correspond to a type-2 membrane protein in which the transmembrane domain (TM in FIG. 3) exists in the region of the 16th to 29th amino acid residues on the N-terminals. Search of this sequence with gene data base in GenBank showed no high homology with any of the data therein. However, with regard to the sialyl-motifs (L and S) in the sialyltransferase homologous region existing in the central part and C-terminal region of the sequence for sialyltransferase, relatively high homology was recognized although some substitution was observed (FIG. 4). The sialyltransferases used for comparison were eleven (11) species, i.e., ST3N-1 (Biochem. Biophys. Res. Commun., 194, 375–382, 1993) ST3N-2 (J. Biol. Chem., 268, 22782–22787, 1993), ST3O-1 (J. Biol. Chem., 269, 17872–17878, 1994), ST3O-2 (Eur. J. Biochem., 247, 558–566, 1997), SThM (GenBank™ database, accession number U14550), ST6N (J. Exp. Med., 172, 641–643, 1990), SAT-II (Proc. Natl. Acad. Sci. U.S.A., 91, 7952–7956, 1994), STX (J. Biol. Chem., 270, 22685–22688, 1995), ST8SiaIII (GenBank™ database, accession number AF004668), PST-1 (Proc. Natl. Acad. Sci. U.S.A., 92, 7031–7035, 1995), ST8SiaV (Biochem. Biophys. Res. Corun., 235, 327–330, 1997). The results suggest that SAT-I which is encoded by the insert 4C7 in pCEV4C7 belongs to the sialyltransferase family. In SAT-I encoded by the DNA, a characteristic amino acid substitution (substitution of histidine for aspartic acid) at 177th amino acid in the sialylmotif L, compared with other sialyltransferases. Further, the amino acid sequence indicates existence of two consensus sequences of the N-glycosylation site (Δ in FIG. 3).

(5) $G_{M3}$, Synthesis in Cells Expressing SAT-I cDNA pCEV4C7 obtained by incorporating the above-mentioned SAT-I-encoding cDNA (4C7) into expression vector pCEV18 was transfected to 3LL-HK46 cells and 3LL-ST28 cells by an electroporation method and the $G_{M3}$ synthase activity of the cells after 48-hour cultivation was assayed by the following method. As controls, pCEV18 was transfected to 3LL-HK46 cells and 3LL-ST28 cells by the same method. 20 μl of a reaction mixture (pH 6.5) containing 0.1 mM CMP-($^{14}$C)-sialic acid (2×$10^3$ CPM), 0.4 mM lactosylceramide, 0.3% (W/V) Triton CF-54, 10 mM $MgCl_2$, 100 mM sodium cacodylate, 150 μg of the homogenate of host cells to which pCEv4c7 (or control plasmid) was incorporated, and 1 mM sialidase inhibitor (2,3-dehydro-2-deoxy-N-acetylsialic acid (2,3-dehydro-2-deoxy-NeuAc, manufactured by BOEHRTNGER MANNHEIM GMBH) was incubated at 37° C. for 2 hours,and lipid components were purified on SepPak C18 column (manufactured by MERCK CO-). The purified material was evaporated to dryness and charged on a 60HPTLC plate (manufactured by MERCK CO.) for silica gel thin layer chromatography. After development with chloroform/methanol/0.5% aqueous $CaCl_2$ solution (55:45:10:, V/V/V), the layer was treated with orcinol sulfate to develop color and measured of radioactivity incorporated into ganglioside using Fujix BAS2000 Bio Imaging Analyzer (manufactured by FUJI PHOTO FILM CO., LTD.). The results revealed uptake of $^{14}$C by ganglioside $G_{M3}$ and $G_{M3}$ synthesis by SAT-I was detected in the pCEV4C7-transfected cells. This indicated that $G_{M3}$ synthesis by SAT-I occurred.

The $G_{M3}$ synthase activity was high at pH 6.0 to 7.0, particularly at around pH 6.5 and increased at least 1.5 times in the presence of 10 mM of $Mn^{2+}$.

The 3LL-HK46 cells and the 3LL-ST28 cells were transfected with above-mentioned pCEV4C7. Forty-two hours after transfection, the cells were subjected to fluoroimmunostaining (anti-$G_{M3}$ antibody M2590 and anti-$G_{M3}$ antibody R24 were used as a primary antibody for 3LL-HK46 cells and 3LL-ST28 cells, respectively, and FITC-conjugated anti-mouse IgM antibody or IgG antibody was used as secondary antibody) and distributions of stained cells were determined by flowcytometry. As controls, each of host cells which were transfected with pCEV18 and inmuno-stained was used. The results are shown in FIG. 6. (a) and (b) are 3LL-ST28 cells, and (c) and (d) are 3LL-HK46 cells. (a) and (c) are transfected with pCEV18 (controls) and (b) and (d) are transfected with pCEV4C7. It is clear that the 3LL-ST28 transfected with plasmid DNA harboring the DNA of the present invention is remarkably stainable. The difficulty of detection of $G_{M3}$ by this method in 3LL-HK46 cells suggests that localization or the like of $G_{M3}$ on the cell surface is different between cell lines.

(6) Expression of SAT-I in Tissues

Expression of SAT-I in tissues or the like was determined by Northern blot analysis. Namely, MTN blos (Clontech) were used, and a 2,066-bp fragment which was excised from the pCEV4C7 with EcoRI was prepared by agarose gel electrophoresis, and radiolabeled with [α-$^{32}$P]dCTP by a usual method, to prepare a radiolabeled probe. A radiolabeled human glyceraldehyde-3-phosphate dehydrogenase gene probe also was used as an internal control for normalizing the amount RNA in each sample. The analysis showed that SAT-I highly expressed in brain, placenta, skeletal muscle and prostate, whereas it was very weakly expressed in liver, kidney, pancreas and colon. In brain, placenta, lung, skeletal muscle, spleen and peripheral blood leukocytes, a minor band of 7 kilobases was detected.

To characterize in more detail the expression of SAT-I in brain, Northern blotting analysis of cerebellum, cerebral cortex, medulla, occipital pole, frontal lobe, temporal lobe, putamen and spinal cord of brain was performed with the same probe. The analysis showed that SAT-I relatively highly expressed over the whole brain, but slightly elevated expression was observed in cerebral cortex, temporal lobe and putamen.

What is claimed is:

1. An isolated DNA which has a nucleotide sequence shown by SEQ ID NO: 1.

2. A recombinant vector comprising the DNA comprising a nucleotide sequence shown by SEQ ID NO: 1.

3. A transformant into which a DNA is introduced, and in which the DNA can be expressed, said DNA comprising a nucleotide sequence shown by SEQ ID NO: 1.

* * * * *